United States Patent
Nazzal et al.

(10) Patent No.: US 12,232,947 B2
(45) Date of Patent: Feb. 25, 2025

(54) IVC FILTER RETRIEVAL DEVICE

(71) Applicant: The University of Toledo, Toledo, OH (US)

(72) Inventors: Munier Nazzal, Toledo, OH (US); Abdullah Nasif, Toledo, OH (US); Mohamed Fikri Mohamed Osman, Toledo, OH (US); Ayman Ahmed, Toledo, OH (US); Sakeena Davis, Toledo, OH (US); Soheila Alidad, Toledo, OH (US); Zahra Alzaher, Toledo, OH (US); Ghayth M. Ansarei, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 17/944,622

(22) Filed: Sep. 14, 2022

(65) Prior Publication Data

US 2024/0081969 A1    Mar. 14, 2024

Related U.S. Application Data

(60) Provisional application No. 63/244,453, filed on Sep. 15, 2021.

(51) Int. Cl.
*A61F 2/01* (2006.01)

(52) U.S. Cl.
CPC ............ *A61F 2/011* (2020.05); *A61F 2/0105* (2020.05)

(58) Field of Classification Search
CPC .............. A61F 2/011; A61F 2/0105; A61F 2002/9528; A61F 2/01; A61F 2/0108; A61F 2/012; A61F 2/013; A61F 2002/016; A61F 2002/018; A61B 2017/22035; A61B 17/221; A61B 2017/2212; A61B 2017/2215; A61B 17/50

See application file for complete search history.

(56) References Cited

U.S. PATENT DOCUMENTS

| | | | |
|---|---|---|---|
| 2004/0059324 A1* | 3/2004 | Francischelli | A61B 18/1445 606/41 |
| 2006/0247572 A1* | 11/2006 | McCartney | A61B 8/0841 604/19 |
| 2009/0299344 A1* | 12/2009 | Lee | A61B 1/00042 606/1 |
| 2014/0172008 A1* | 6/2014 | McKinnis | A61B 17/50 606/200 |
| 2017/0348013 A1* | 12/2017 | Mottola | A61B 17/22031 |
| 2019/0298323 A1* | 10/2019 | Lambrecht | A61B 17/00 |
| 2020/0093584 A1* | 3/2020 | Chaar | A61F 2/011 |
| 2020/0330112 A1* | 10/2020 | Verma | A61B 17/221 |

* cited by examiner

*Primary Examiner* — Brooke Labranche
(74) *Attorney, Agent, or Firm* — MacMillan, Sobanski & Todd, LLC

(57) ABSTRACT

An IVC filter retrieval device useful for removing an IVC filter from a blood vessel, and useful for removing a tilted IVC filter causing the hook to be embedded in the side (wall) of a blood vessel from the blood vessel, and methods for using the same are described. The IVC retrieval device can be used to retrieve other foreign bodies such as, but not limited to, catheters and wires that may become detached from their devices and released into the blood vessels.

13 Claims, 28 Drawing Sheets

IVC FILTER RETRIEVAL DEVICE

RELATED APPLICATIONS

This application claims priority to U.S. Provisional Application No. 63/244,453 filed under 35 U.S.C. § 111(b) on Sep. 15, 2021, the disclosure of which is incorporated herein by reference in its entirety.

STATEMENT REGARDING FEDERALLY SPONSORED RESEARCH

This invention was made with no government support. The government has no rights in this invention.

BACKGROUND

Inferior vena cava (IVC) filters are small, metal devices temporarily placed in the inferior vena cava that are designed to catch blood clots and stop the blood clots from traveling to lungs. These filters are needed in patients with a history or risk of deep vein thrombosis (DVT) or pulmonary embolism (PE), as well as trauma victims and immobile patients Immobile patients may need IVC filters when other methods such as blood thinning agents are unsuccessful.

In terms of removing an IVC filter, there are several retrieval methods in practice. However, conventional methods for retrieving IVC filters are not always effective or cost efficient. The snare method is the most popular method of retrieval, and relies on the ability to grasp the retrieval hook on the end of the IVC filter. However, when the IVC filter is tilted at an angle, the snare is unable to grab the retrieval hook by itself. Additionally, the surgeon and/or radiologist needs to be able to see the hook clearly on the angiogram, which is a black and white two-dimensional image. These variables make the retrieval process more difficult and can significantly increase retrieval time. If a surgeon or radiologist has to attempt multiple methods of IVC filter retrieval, the health of the patient is at risk due to extended sedation. More invasive methods such as the use of forceps yield an increased recovery time for the patient.

An average of 65,000 IVC filters are placed annually in the United States. About 15% of the time, the IVC filter becomes embedded in the intima of the vessel, rendering it irretrievable by conventional methods such as the snare method. Current IVC filter retrieval devices are inefficient in adverse conditions, resulting in increased patient risks, lost time, and money. Thus, there is a need in the art for new and improved devices and methods for retrieving IVC filters.

SUMMARY

Provided herein is a foreign body retrieval and IVC filter retrieval device comprising a sheath defining a lumen and extending from a sheath proximal end to a sheath distal end; a grabbing member movable within the lumen, wherein the grabbing member extends from a distal grabbing member end to a proximal grabbing member end, and includes a distal grabbing member portion; a closing member movable within the lumen, wherein the closing member extends from a distal closing member end to a proximal closing member end; wherein the grabbing member is configured to move between an extended grabbing position in which the distal grabbing member end protrudes from the sheath at the sheath distal end, and a retracted grabbing position in which the distal grabbing member end is disposed within the sheath; wherein the closing member is configured to move between an extended closing position in which the distal closing member end protrudes from the sheath at the sheath distal end, and a retracted closing position in which the closing member is disposed within the sheath; wherein the grabbing member and the closing member are movable to create a closed loop wherein the distal grabbing member end is in direct contact with the distal closing member end; and wherein the grabbing member and the closing member are movable to create an open loop wherein the distal grabbing member end is disposed a distance away from the distal closing member end, the distance defining a gap.

In certain embodiments, the distal grabbing member end is rotatable by rotating the proximal grabbing member end.

In certain embodiments, the distal closing member portion comprises a curved protrusion causing the distal closing member end to protrude outward a distance from an axis defined by the proximal closing member end. In particular embodiments, a loop formed between the grabbing member and the closing member has a loop radius larger than a radius of the sheath.

In certain embodiments, the IVC filter retrieval device further comprises a computer or microcontroller configured to control movement of the grabbing member and the closing member so as to form an open loop or a closed loop between the grabbing member and the closing member.

In certain embodiments, the IVC filter retrieval device further comprises a spacer between the closing member and the grabbing member configured to maintain a minimum distance between the closing member and the grabbing member.

In certain embodiments, each of the distal grabbing member end and the distal closing member end includes a magnet configured to attract each other.

In certain embodiments, the distal grabbing member portion has a curvature, defining an arc or semicircle. In certain embodiments, the distal grabbing member portion is a hook. In certain embodiments, the distal grabbing member portion defines a partial square or a partial rectangle.

In certain embodiments, the grabbing member and the closing member are movable to create the closed loop while each of the grabbing member and the closing member is retracted within the sheath.

In certain embodiments, the grabbing member and the closing member are movable to create the closed loop while each of the grabbing member and the closing member protrudes from the sheath at the sheath distal end.

Further provided is a method for retrieving an IVC filter from a blood vessel, the method comprising inserting an IVC filter retrieval device described herein into the blood vessel in proximity to the IVC filter; moving the grabbing member into the extended grabbing position; positioning the grabbing member so as to grab the IVC filter with the distal grabbing member end and secure the IVC filter on the distal grabbing member portion; moving the grabbing member into the retracted grabbing position; and retrieving the IVC filter retrieval device from the blood vessel to retrieve the IVC filter.

In certain embodiments, the method further comprises moving the closing member into the extended closing position, and moving the grabbing member and the closing member to create the closed loop, before moving the grabbing member into the retracted grabbing position.

In certain embodiments, the method further comprises moving the grabbing member and the closing member to create the closed loop after moving the grabbing member into the retracted grabbing position.

In certain embodiments, the IVC filter is grabbed at an IVC filter neck instead of an IVC filter hook.

Further provided is a method of retrieving an IVC filter from a blood vessel, the method comprising inserting an IVC filter retrieval device into the blood vessel in proximity to the IVC filter; moving an arcuate end of a first elongated member of the device so as to grab the IVC filter and capture the IVC filter on the arcuate end; creating a closed loop between the first elongated member and a second elongated member of the device so as to secure the IVC filter for retrieval; retracting the first elongated member and the second elongated member into a sheath; and retrieving the IVC filter retrieval device from the blood vessel so as to retrieve the IVC filter.

In certain embodiments, the closed loop is created after retracting the first elongated member and the second elongated member into the sheath.

In certain embodiments, a radius of the closed loop is larger than a radius of the sheath.

In certain embodiments, the IVC filter is grabbed at an IVC filter neck instead of an IVC filter hook.

The IVC filter retrieval device described herein can be used to retrieve other foreign bodies within the vessels such as, but not limited to, wires and catheters.

BRIEF DESCRIPTION OF THE DRAWINGS

FIG. 3 shows IVC filter retrieval device with an enlarged grabbing member portion to provide an enhanced ability to contact and secure an IVC filter within a vessel.

DETAILED DESCRIPTION

Figure 1:
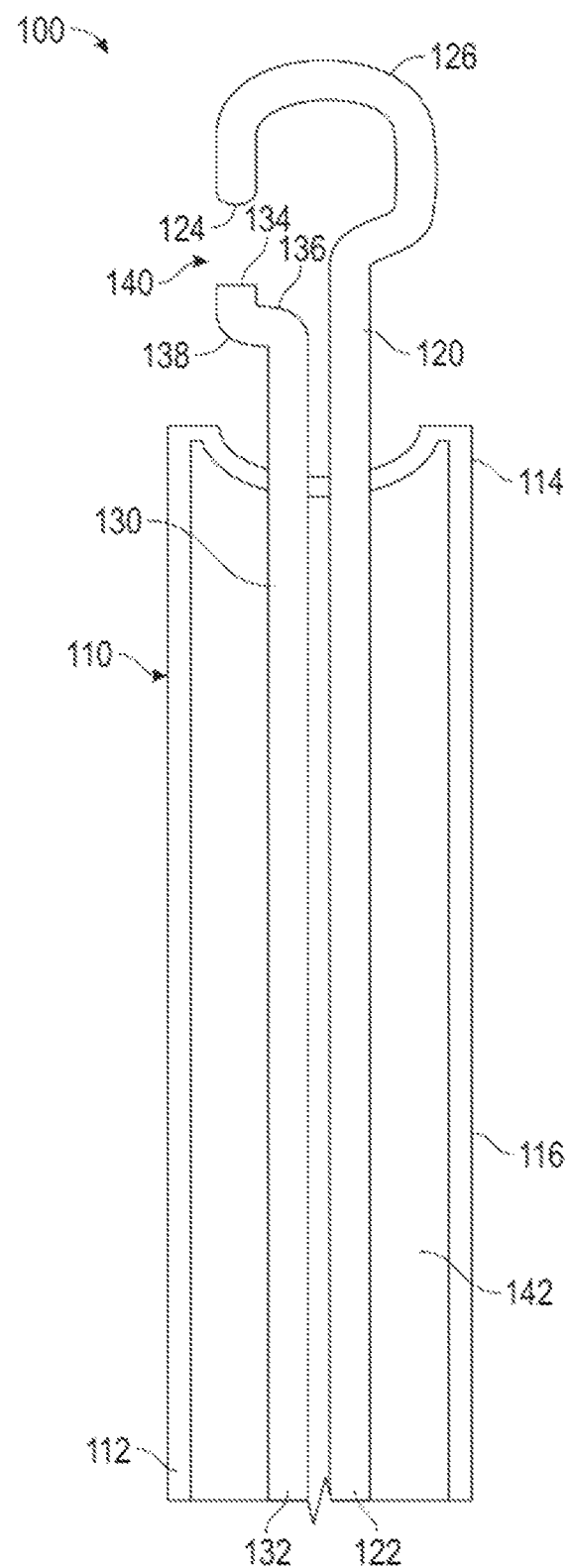
FIG. 1: Illustration of a first embodiment of an IVC filter retrieval device with a closing member and a grabbing member that are in a deployed state and an open loop configuration, protruding from the sheath.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Provided herein is an IVC filter retrieval device configured to safely remove an IVC filter, including an IVC filter that is embedded in the intima of a vessel, in an efficient and cost effective manner. In some embodiments, the IVC filter retrieval device is characterized by a hook deployed from a sheath and capable of forming a closed loop. The hook on the IVC filter retrieval device is designed to be large enough to secure the retrieval hook of the IVC filter and/or the neck portion of the IVC filter. This is ideal in cases when conventional methods, such as snares and forceps, are not successful. When the hook is deployed/embedded into the vessel, the surgeon is able to rotate around the entire circumference of the vessel until the IVC filter retrieval device engages with the IVC filter at the hook or the neck of the filter. The hook securely grabs the IVC filter and pulls it away from the intima of the vessel and into the retrievable sheath or to a position within the vessel that allows easier manipulation and retrieval. The hook can sweep around the entire boundary of the vessel until the IVC filter retrieval device makes contact with the IVC filter, at which point the IVC filter can be retrieved. The IVC filter retrieval device does not require the surgeon to specifically aim for only one IVC filter hook, which is a tiny target of just a few millimeters. Rather, advantageously, making initial contact with the neck portion or even a leg of the IVC filter may still result in successful retrieval of the IVC filter.

Referring now to FIGS. 1-17, a non-limiting example embodiment of an IVC filter retrieval device 100 is depicted. The IVC filter retrieval device 100 may include a sheath 110, a grabbing member 120, and a closing member 130. The IVC filter retrieval device 100 may also include other components. The sheath 110 may have a sheath proximal end 112, a sheath distal end 114, and a sheath middle portion 116 that extends between the sheath proximal end 112 and the sheath distal end 114. The sheath 110 defines a lumen 142 therein, and the grabbing member 120 and the closing member 130 are movable within the lumen 142, both proximally and distally, as well as rotatably. The sheath 110 is composed of a material suitable for insertion into blood vessels, such as, but not limited to, silicone or polyurethane. The sheath 110 can be between 6-8 Fr, for example. However, other sizes of the sheath 110 are possible and encompassed within the scope of the present disclosure.

Referring still to FIGS. 1-17, the grabbing member 120 is an elongated member having a proximal grabbing member end 122, a distal grabbing member end 124, and a distal grabbing member portion 126. The distal grabbing member portion 126 may be in the form of a hook or otherwise have a curvature or the shape of an arc or semicircle, as shown in FIGS. 1-17. However, alternatively, the distal grabbing member portion 126 may have a shape that more resembles a square or rectangle, such as a partial square or partial rectangle. The grabbing member 120 may be composed of any rigid material suitable for insertion into blood vessels and sterilizable, such as, but not limited to, stainless steel. However, any appropriate material that is acceptable for use in medical devices can be used. The grabbing member 120 can be flexible or have minimal flexibility depending on the desired use.

Figure 2:
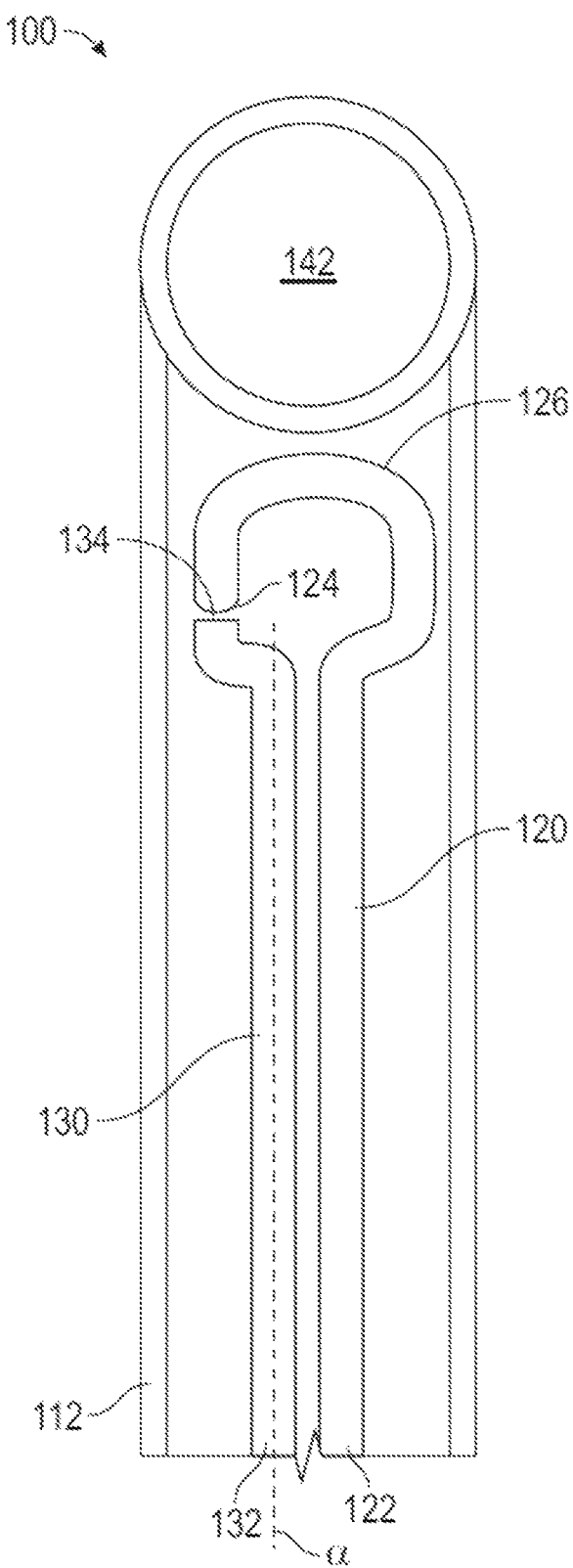
FIG. 2: Illustration of the first embodiment of an IVC filter retrieval device with a closing member and a grabbing member that are retracted within the sheath.
Figure 3:
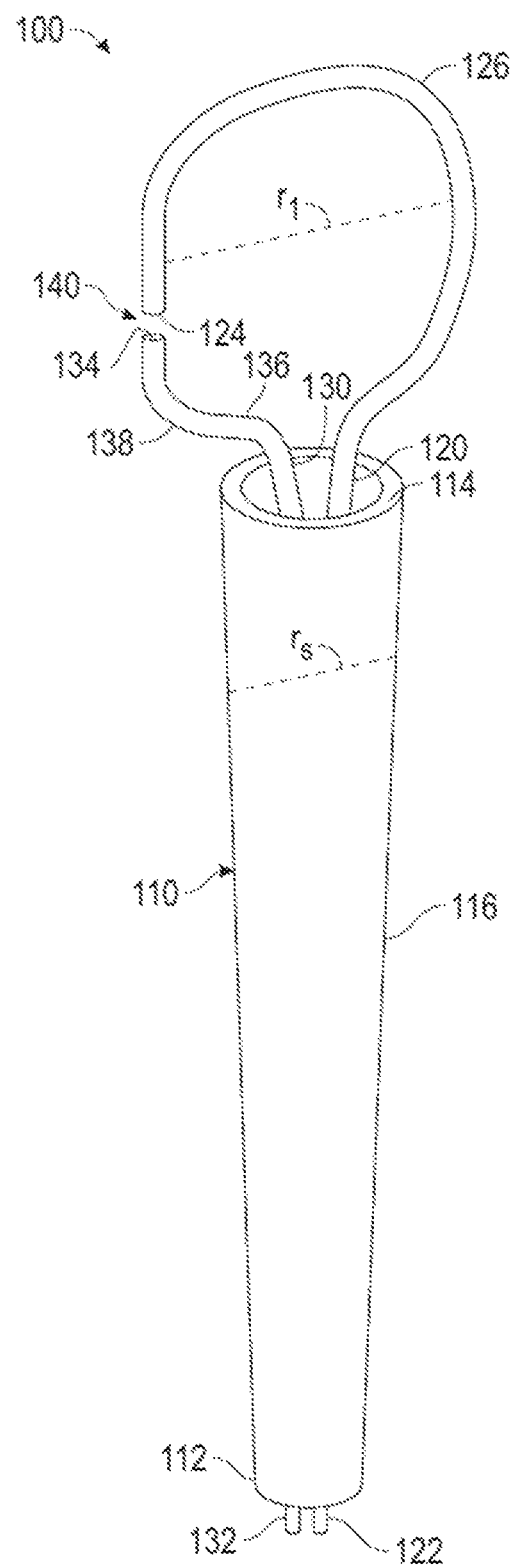
FIG. 3: Illustration of the first embodiment of an IVC filter retrieval device with a loop radius larger than a sheath radius, and with a closing member and a grabbing member that are partially engaged, having a small gap between them.

Referring still to FIGS. 1-17, the closing member 130 is an elongated member having a proximal closing member end 132, a distal closing member end 134, and a distal closing member portion 136. The distal closing member portion 136 may also have a curved protrusion 138 causing the distal closing member end 134 to protrude outward (i.e., toward the sheath 110) some distance from an axis a defined by the proximal closing member end 132, as depicted in FIG. 2. Advantageously, the curved protrusion 138 allows for an enlarged grabbing member portion 126, and therefore an enlarged loop structure or hook capable of grabbing and securing an IVC filter 150. In particular, the curved protrusion 138 allows for the grabbing member 120 and the closing member 130 to form a closed loop having a loop radius $r_l$ larger than the radius $r_s$ of the sheath 110, such as depicted in FIG. 3. Utilizing a somewhat flexible material to form the grabbing member 120 also aids in making the loop radius $r_l$ larger than the sheath radius $r_s$. However, though the curved protrusion 138 allows for the loop radius $r_l$ to be larger than the sheath radius $r_s$, it is not necessary that the loop radius $r_l$ be larger than the sheath radius $r_s$. For example, FIGS. 1-2 depict the IVC filter retrieval device 100 where the loop radius $r_l$ is not larger than the sheath radius $r_s$. In any event, the closing member 130 may be composed of any rigid material suitable for insertion into blood vessels and sterilizable, such as, but not limited to, stainless steel. However, any appropriate material that is suitable for use in medical devices can be used. The closing member 130 can be flexible or have minimal flexibility depending on the desired use.

Referring again to FIGS. 1-17, the sheath 110 defines a lumen 142 inside of which the grabbing member 120 and the closing member 130 can move and rotate, and out of which the distal grabbing member portion 126 and the distal closing member portion 136 can protrude at the sheath distal end 114 for grabbing and securing an IVC filter 150. The proximal grabbing member end 122 may protrude from the proximal sheath end 112, leaving the proximal grabbing member end 122 exposed for a user to rotate, push, or pull, so as to rotate or move the distal grabbing member portion 126 and the distal grabbing member end 124. The proximal closing member end 132 may also protrude from the proximal sheath end 112, leaving the proximal closing member end 132 exposed for a user to rotate, push, or pull, so as to rotate or move the distal closing member portion 136 and the distal closing member end 134. As noted above, the distal grabbing member portion 126 may have a curvature so as to have a structure in which the distal grabbing member end 124 may terminate near the distal closing member end 134, and the grabbing member 120 is movable in conjunction with the closing member 130 so as to have the distal grabbing member end 122 directly contact the distal closing member end 134 to thereby form a closed loop.

Referring still to FIGS. 1-17, the closing member portion 136 may not only allow for a larger closed loop structure to be formed, but the closing member portion 136 can also help the distal closing member end 134 align with the grabbing member distal end 124. Such alignment may be achieved by rotating the grabbing member 120 and/or the closing member 130. Once aligned, the distal closing end 134 may come in contact with the distal grabbing member end 124 so as to create a closed loop when the distal closing end 134 is pushed toward the distal grabbing member end 124 and/or the distal grabbing member end 124 is pulled toward the distal closing end 134. The distal grabbing end 124 can come in contact with the distal closing end 134 so as to create a closed loop when the distal grabbing end 124 is pulled toward the distal closing end 134. The distal closing end 134 and the distal grabbing end 124 can also form a gap 140 between the ends 124, 134. The gap 140 can vary in size according to a desired use.

The distal grabbing member end 124 and the distal closing member end 134 can have a mechanism of attachment whereby the two distal ends 124, 134 are prevented from coming apart, so as to prevent an IVC filter 150 from dislodging easily. For example, referring now to FIG. 7, the distal grabbing member end 124 and the distal closing member end 134 may include magnets 148a, 148b configured to attract each other to facilitate alignment and closing between the distal ends 124, 134. The distal closing member end 134 and the distal grabbing member end 124 may also be engaged together by any means such as, but not limited to, a spring system, a hydraulic system, or a tension system.

Referring again to FIGS. 1-17, the grabbing member 120 and the closing member 130 can also form a partial loop in which the grabbing member 120 and the closing member 130 create a loop with only a small gap 140 between the distal grabbing member end 124 and the distal closing member end 134. As discussed in more detail below, in use, the grabbing member 120 and the closing member 130 can engage to form a closed loop prior to retracting the grabbing member 120 and the closing member 130 into the sheath 110, after retracting the grabbing member 120 and the closing member 130 into the sheath 110, or not at all. In some cases, it may be desirable to engage the closing member 130 and the grabbing member 120 to form only a partial loop instead of a closed loop at some point during the retrieval process.

Figure 6:
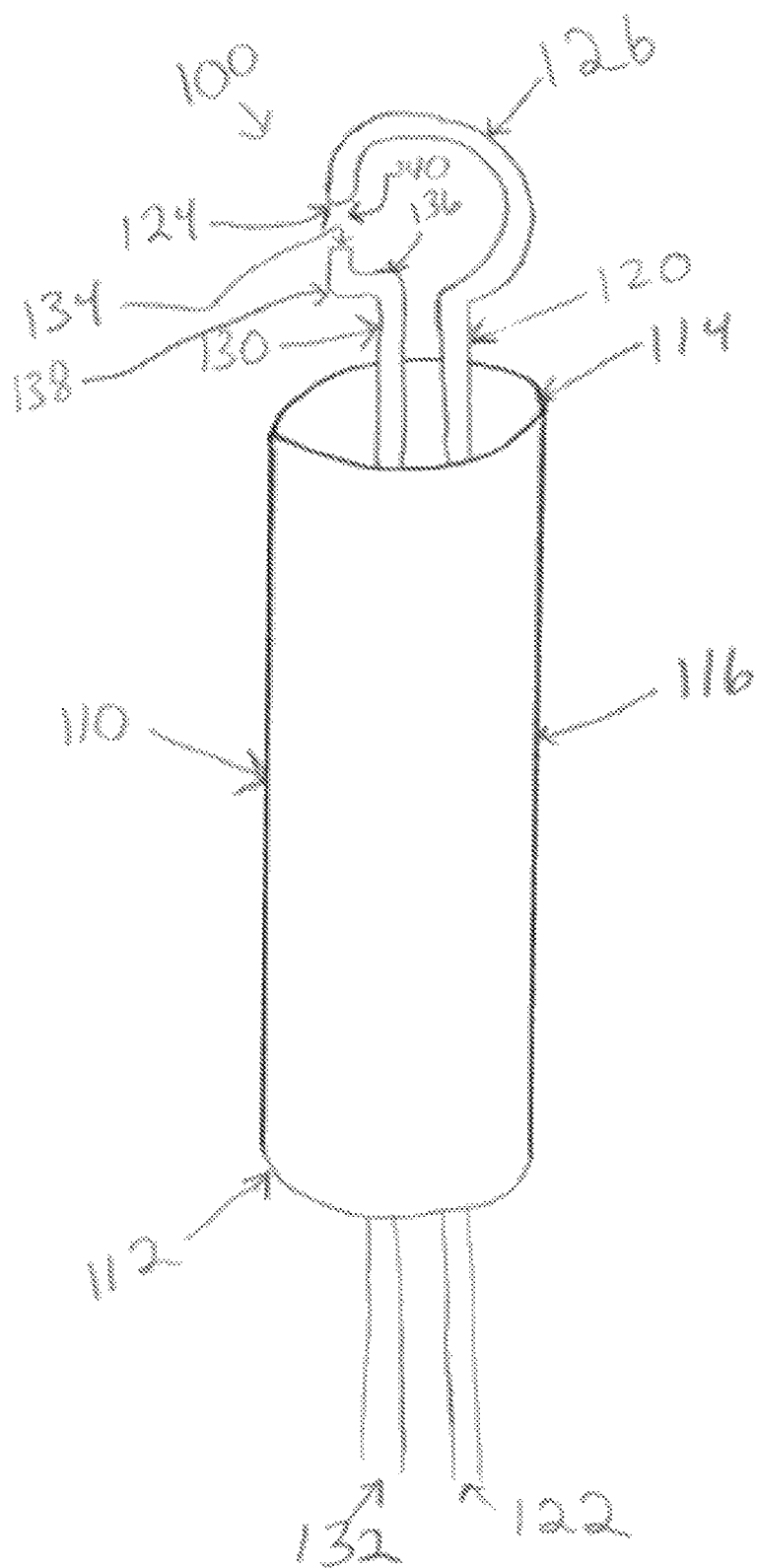
FIG. 6: Illustration of a first embodiment of an IVC filter retrieval device with a closing member and a grabbing member that are partially engaged, with a small gap between them.

Referring now to FIG. 6, the IVC filter retrieval device 100 is depicted partially closed, creating a loop with a small gap 140. This may be a final engagement position, or it may represent a moment in which the closing member 130 and the grabbing member 120 are currently being engaged towards the other member 120, 130 so as to have the distal grabbing member end 124 and the distal closing member 134 approaching one another. Having only a small gap 140 provides the benefit of allowing reattachment to the IVC filter 150 if the IVC filter 150 becomes dislodged and the members 120, 130 cannot be adjusted for any reason. This prevents the user from having to remove the device 100 and use a new device in order to remove the IVC filter 150. However, the small gap 140 still provides the added security of enhanced gripping of the IVC filter 150, thereby decreasing the chance the IVC filter 150 may be dislodged.

Figure 7:
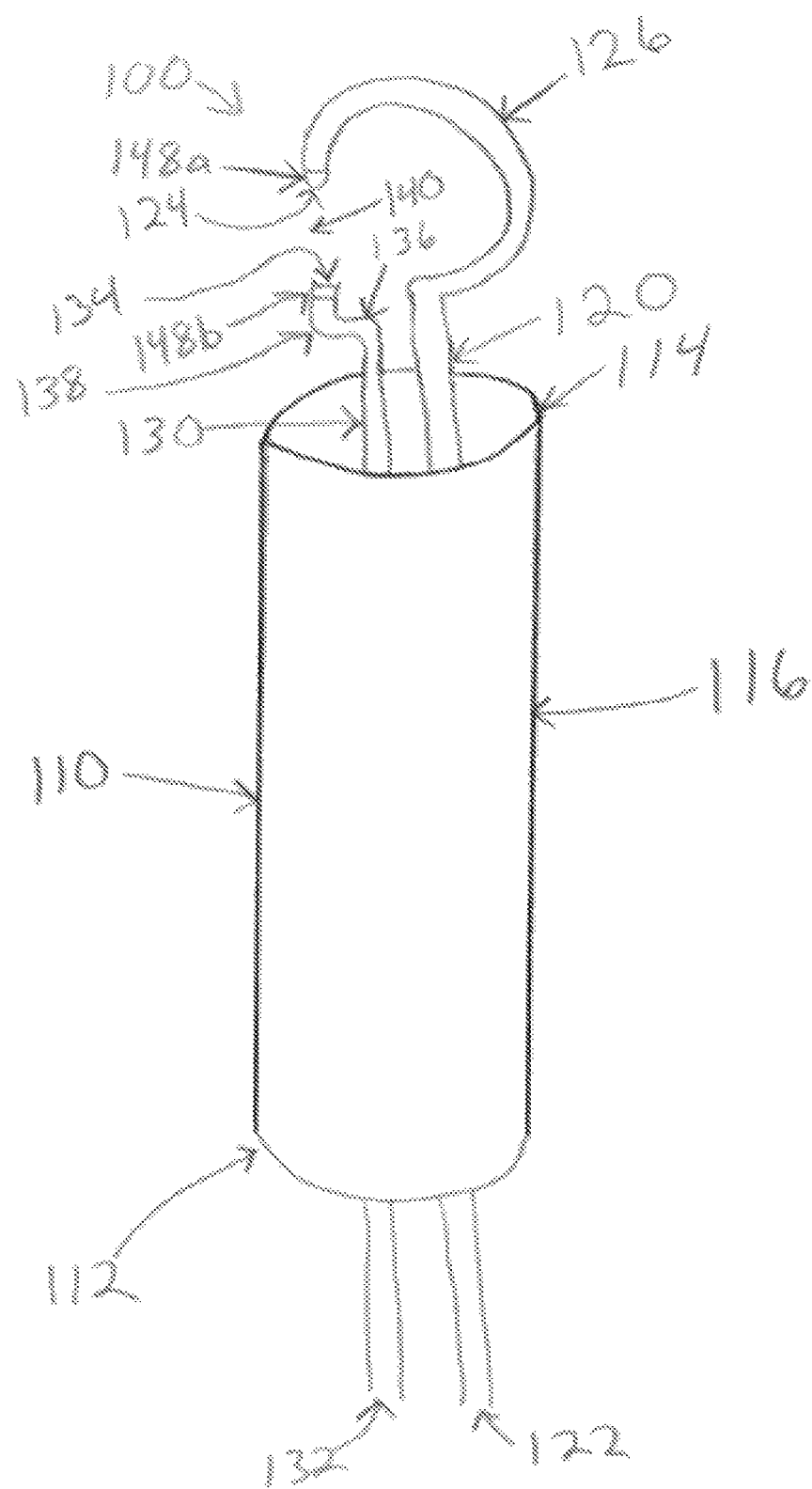
FIG. 7: Illustration of the first embodiment of an IVC filter retrieval device with a closing member and a grabbing member that are not in direct contact.

Referring now to FIG. 7, the distal grabbing member end 124 and the distal closing member end 134 may be disposed at a distance from each other so as to create an open loop with a larger gap 140 between the distal grabbing member end 124 and the distal closing member end 134. The gap 140 can vary in size according to a desired usage of the system.

Figure 8:
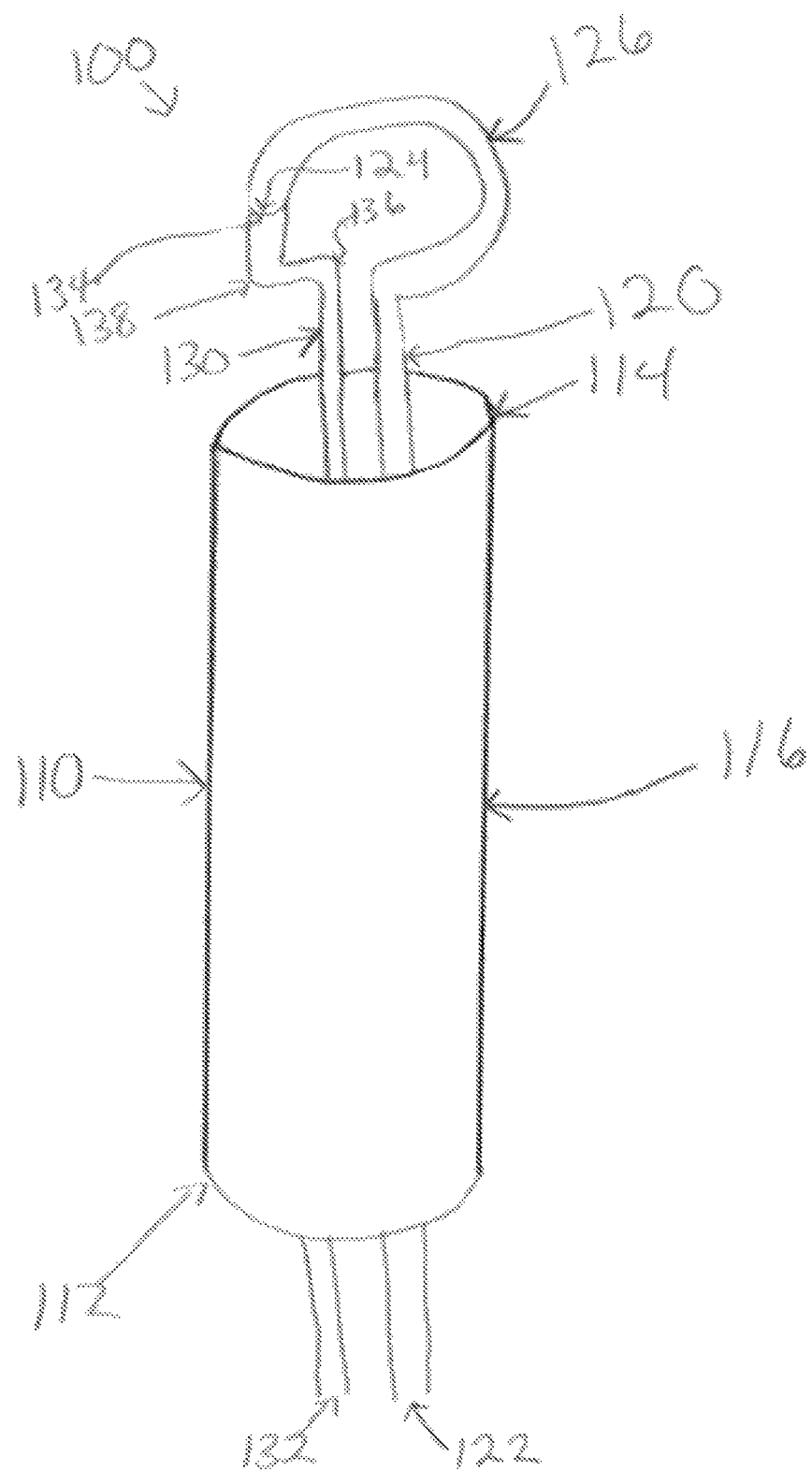
FIG. 8: Illustration of the first embodiment of an IVC filter retrieval device with a closing member and a grabbing member that are in direct contact so as to form a closed loop.

Referring now to FIG. 8, the distal closing member end 134 and the distal grabbing member end 124 may be engaged and in direct contact with each other, so as to form a closed loop. In this configuration, the closed loop formed from the distal closing member end 134 and the distal grabbing member end 124 being in direct contact with one another prevents the dislodgment of an IVC filter 150 that is engaged by the grabbing member 120.

Figure 9:
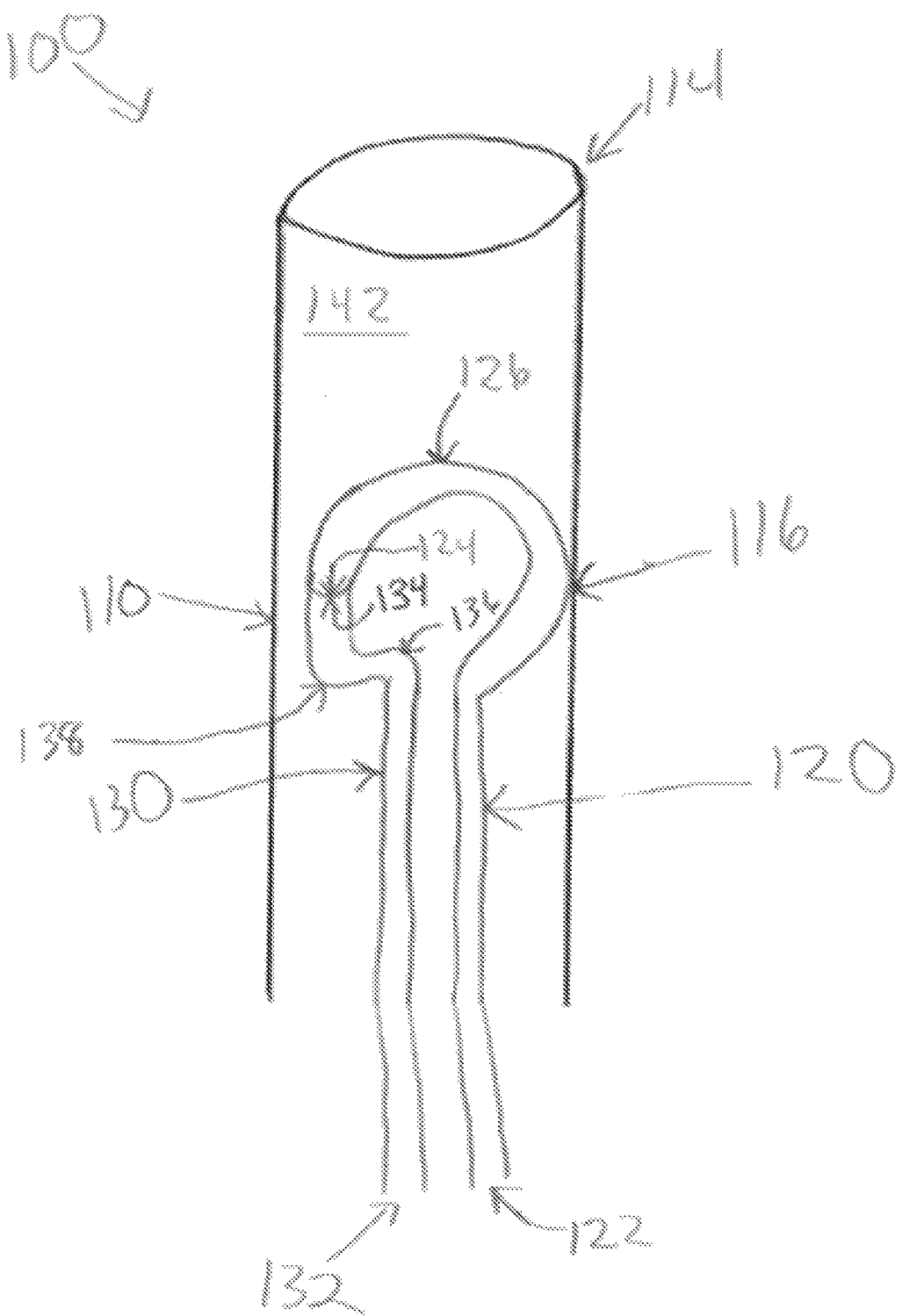
FIG. 9: Illustration of the first embodiment of an IVC filter retrieval device with a closing member and a grabbing member that are in direct contact at the respective distal ends, where the closing member and the grabbing member are retracted within the sheath.

Referring now to FIG. 9, the distal grabbing member portion 126 and the distal grabbing member end 124, along with the distal closing member portion 136 and the distal closing member end 134, may be retracted into the lumen 142 of the sheath 110. This retraction of the closing member 130 and the grabbing member 120 into the sheath 110 can be performed before or after retrieval of an IVC filter 150, allowing the IVC filter retrieval device 100 to be removed from the vessel without complications. However, in some cases, it may be desirable to not retract the grabbing member 120 and/or the closing member 130 into the sheath 110.

Figure 10:
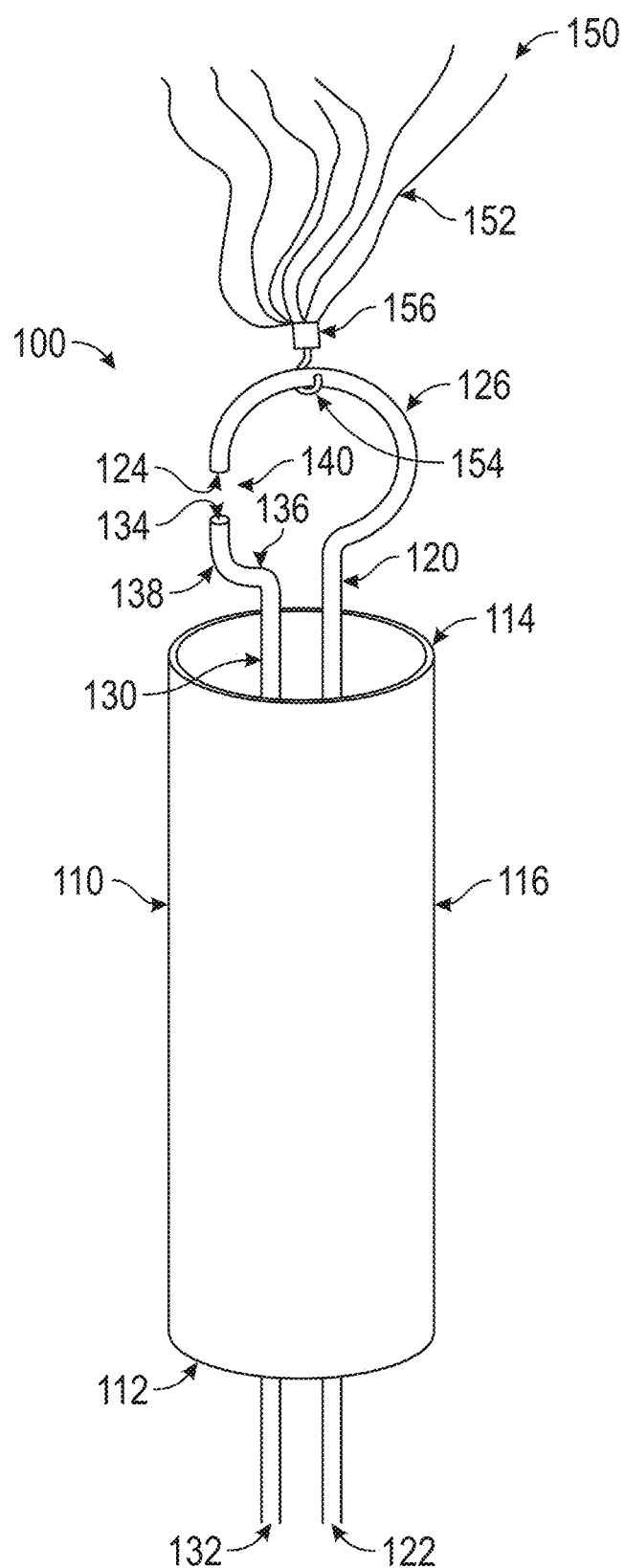
FIG. 10: Illustration of the first embodiment of an IVC filter retrieval device with a closing member and a grabbing member that are not in direct contact, where the grabbing member is grabbing the hook of an IVC filter.

Referring now to FIG. 10, the grabbing member 120 is depicted grabbing an IVC filter 150 at the IVC hook 154. In this illustration, the closing member 130 and the grabbing member 120 are disposed at a distance from each other so as to create an open loop with a gap 140 between the distal grabbing member end 120 and the distal closing member end 134. The grabbing member 120 can be positioned into place near the IVC filter 150, and then to grab the IVC filter 150, by applying a twisting, pulling, and/or pushing motion to the grabbing member 120 and/or the closing member 130 at the proximal grabbing member end 122 and/or the proximal closing member end 132. The grabbing member 120 can be moved accordingly to grab the IVC hook 154 and thereby secure the IVC filter 150 to the IVC filter retrieval device 100.

Figure 11:
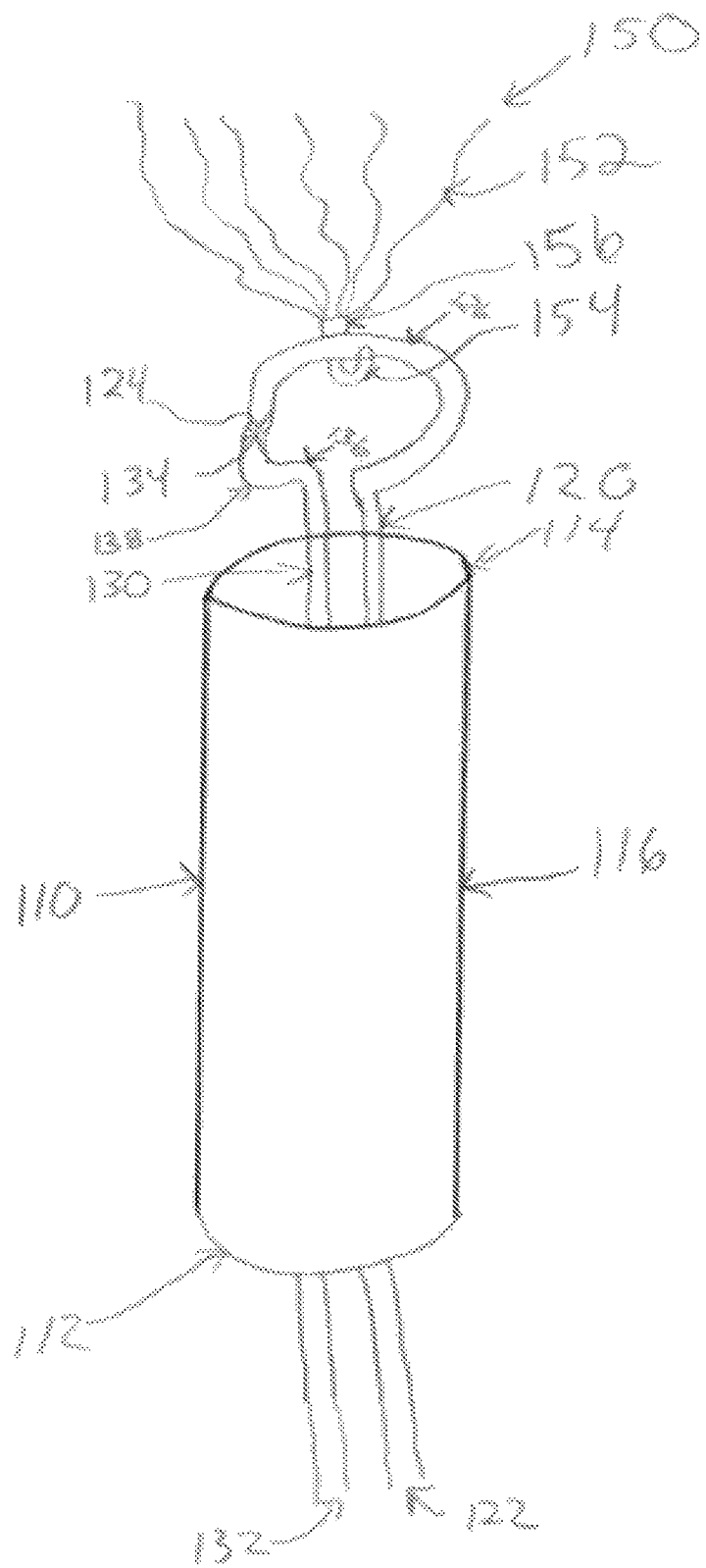
FIG. 11: Illustration of the first embodiment of an IVC filter retrieval device with a closing member and a grabbing member that are in direct contact at their respective distal ends, where the grabbing member is grabbing the hook of an IVC filter.

Referring now to FIG. 11, the grabbing member 120 is depicted grabbing the IVC filter 150 at the IVC hook 154. The engagement and direct contact between the grabbing member 120 and the closing member 130 to form a closed loop makes it less likely that the IVC filter 150 will dislodge upon removal of the IVC filter retrieval device 100 from the vessel. When the grabbing member 120 and the closing member 130 are retracted into the sheath 110, the closed loop prevents the IVC filter 150 from coming loose.

Figure 12:
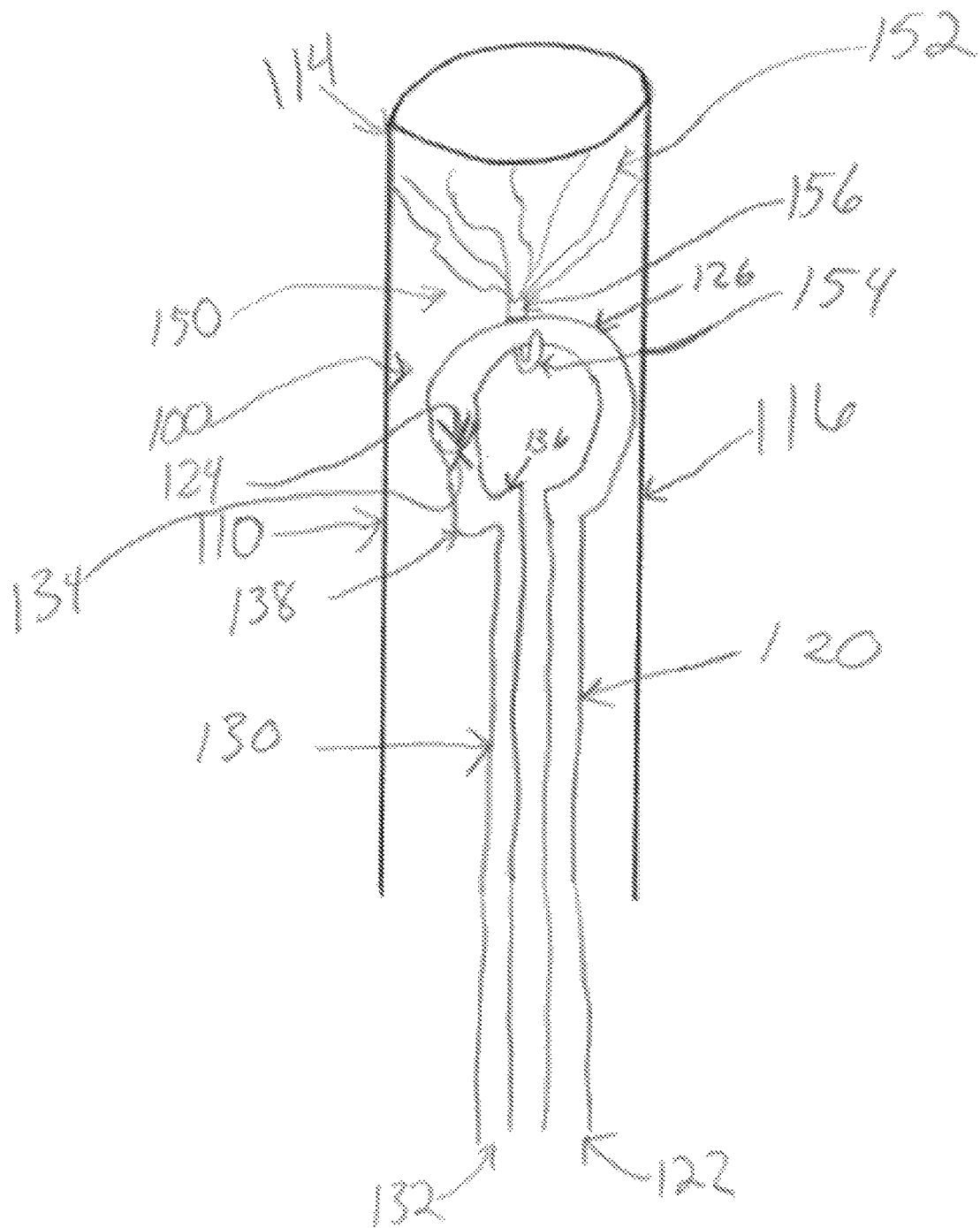
FIG. 12: Illustration of the first embodiment of an IVC filter retrieval device with a closing member and a grabbing member that are in direct contact at their respective distal ends, where the grabbing member is grabbing the hook of an IVC filter, and where the grabbing member and the closing member are retracted within the sheath.

Referring now to FIG. 12, the closing member 130 and the grabbing member 120 may be closed together so as to create a closed loop, and may in the closed loop configuration be retracted into the sheath 110. Notably, the closing member 130 and the grabbing member 120 may also be retracted into the sheath 110 in an open loop configuration. In FIG. 12, the grabbing member 120 is depicted grabbing the IVC filter 150 at the IVC filter hook 154. The engagement between the grabbing member 120 and the closing member 130 makes it less likely that the IVC filter 150 will dislodge while retracted within the sheath 110 and while the IVC filter retrieval device 100 is being retrieved. The retracted members 120, 130 allow the IVC filter retrieval device 100 to be easily removed from the vessel without complications.

Figure 13:
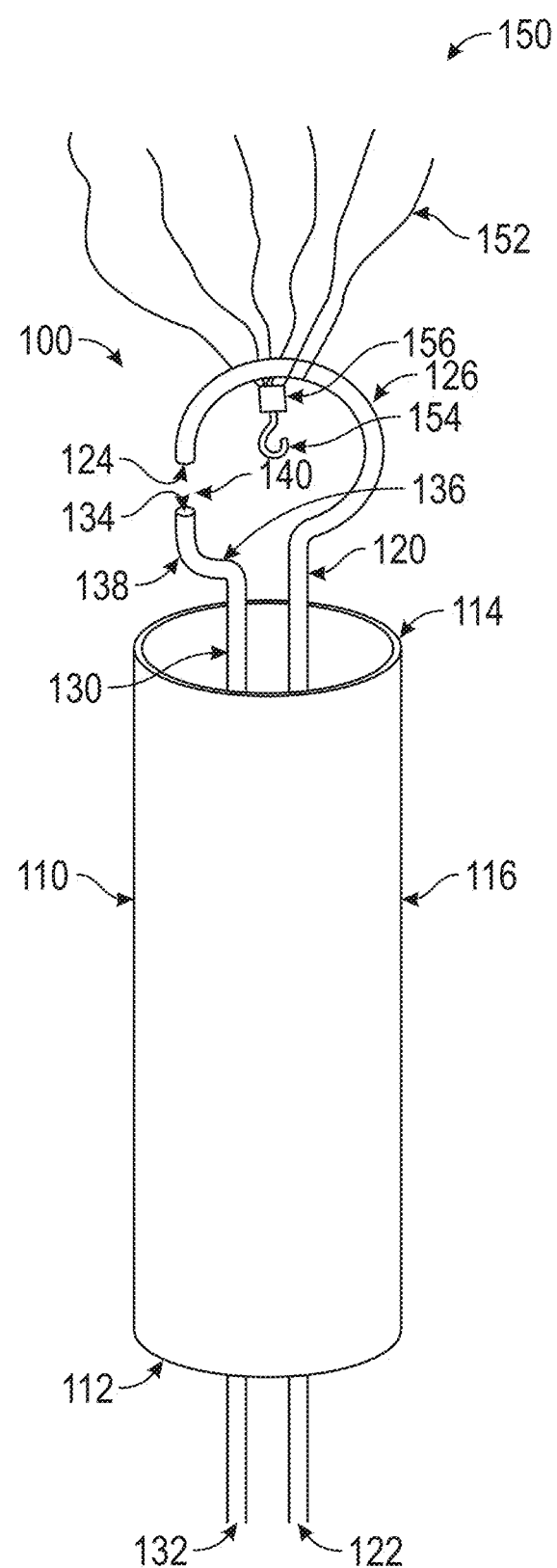
FIG. 13: Illustration of the first embodiment of an IVC filter retrieval device with a closing member and a grabbing member that are not in direct contact, and the grabbing member is positioned nearby the neck of an IVC filter.

Referring now to FIG. 13, the grabbing member 120 is depicted grabbing the IVC filter 150 at the IVC filter neck 156 while the closing member 130 and the grabbing member 120 are disposed at a distance from each other so as to create an open loop with a gap 140 between the distal closing member 134 end and the distal grabbing member end 124. The gap 140 can vary in size according to a desired use of the IVC filter retrieval device 100. This may be needed, for instance, in situations where the IVC filter 150 has become lodged in the wall of a vessel such that the IVC filter hook 154 is not accessible. The grabbing member 120 can be positioned to secure the IVC neck 156, for example, by applying a pushing, pulling, and/or twisting motion to the grabbing member 120 at the grabbing member proximal end 122. In other embodiments, the grabbing member 120 can grab a leg 152 of the IVC filter 150 instead of the IVC filter neck 156 or the IVC filter hook 154.

Figure 14:
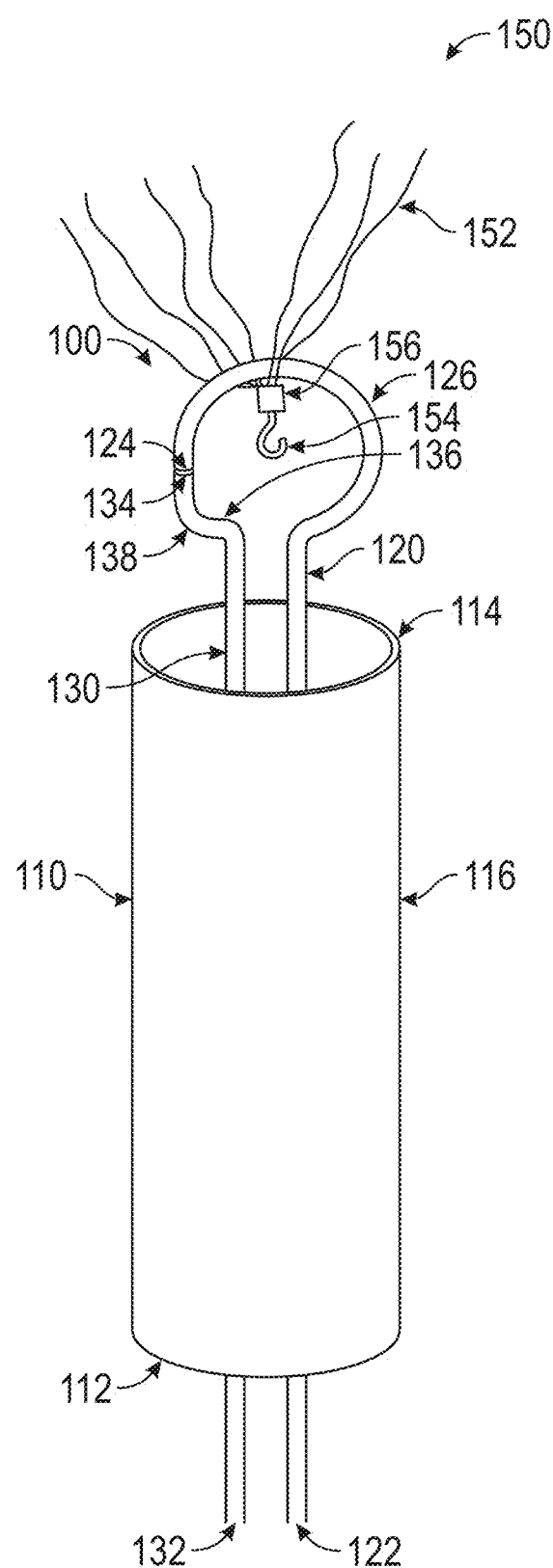
FIG. 14: Illustration of the first embodiment of an IVC filter retrieval device with a closing member and a grabbing member that are in direct contact, and the grabbing member is positioned nearby the neck of an IVC filter.

Referring now to FIG. 14, the grabbing member 120 is depicted grabbing the IVC filter 150 at the IVC filter neck 156 while the closing member 130 and the grabbing member 120 are in direct contact so as to create a closed loop. More specifically, the grabbing member distal end 124 is positioned in direct contact with the closing member distal end 134. The grabbing member 120 can be positioned to secure the IVC filter neck 156, for example, by applying a pushing, pulling, and/or twisting motion to the grabbing member 120 at the grabbing member proximal end 122, and then pulling the grabbing member proximal end 122 and/or pushing the closing member proximal end 132 so as to bring the closing member distal end 134 into contact with the grabbing member distal end 124, and holding the grabbing member 120 and closing member 130 in this position to maintain the closed loop structure. The engagement between the distal grabbing member end 124 and the distal closing member end 134 makes it less likely that the IVC filter 150 will dislodge as the IVC retrieval device 100 is retracted from the vessel with the IVC filter 150.

Figure 15:
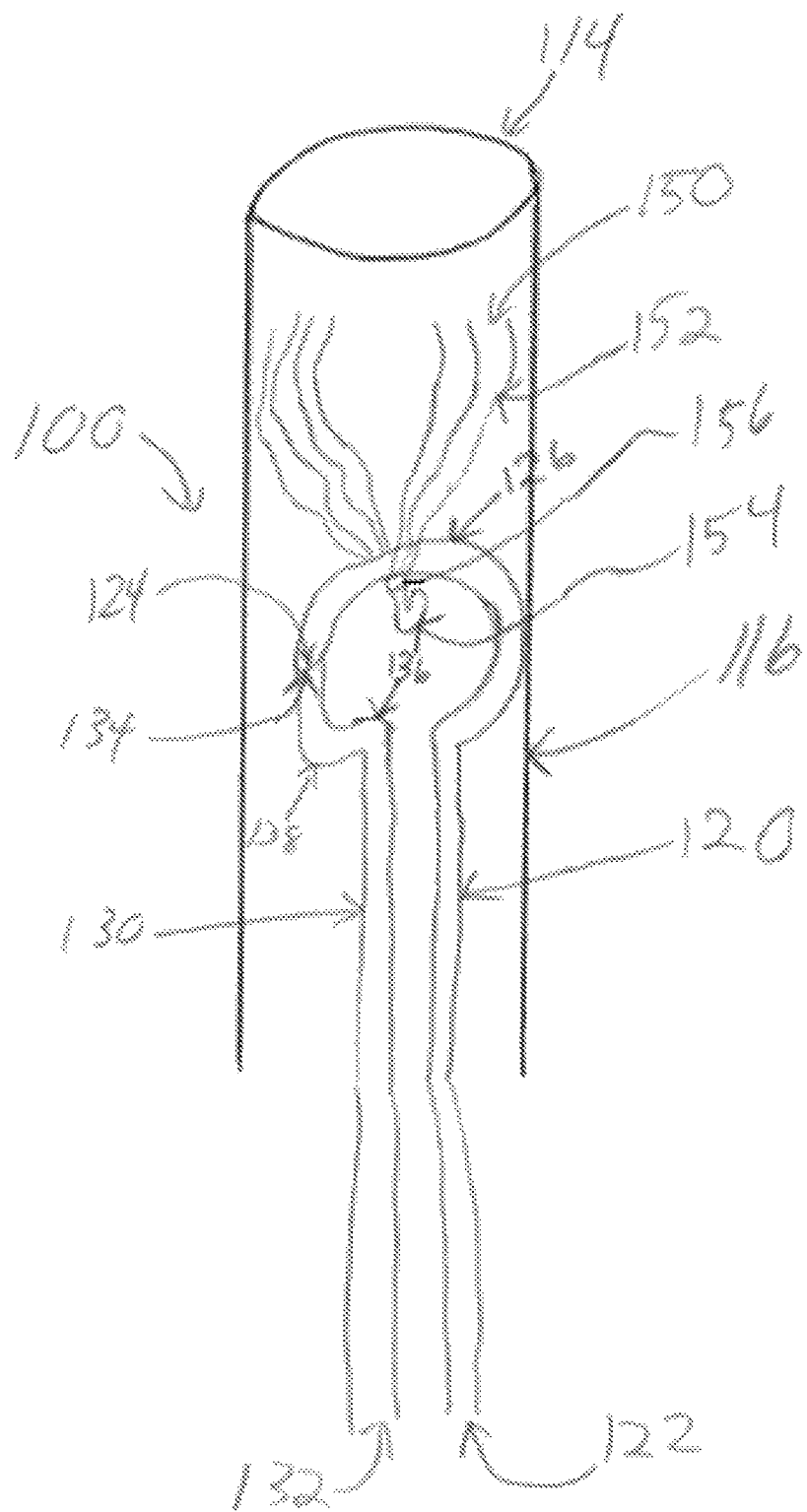
FIG. 15: Illustration of the first embodiment of an IVC filter retrieval device with a closing member and a grabbing member that are in direct contact, where the grabbing member is grabbing the neck of an IVC filter, and the grabbing member and the closing member are retracted within the sheath.

Referring now to FIG. 15, the grabbing member 120 is depicted grabbing the IVC filter 150 at the IVC filter neck 156 while retracted within the sheath 110. The engagement (i.e., direct contact) between the grabbing member 120 and the closing member 130 makes it less likely that the IVC filter 150 will dislodge as the IVC filter retrieval device 100 is retracted into and through the sheath 110.

Figure 16:
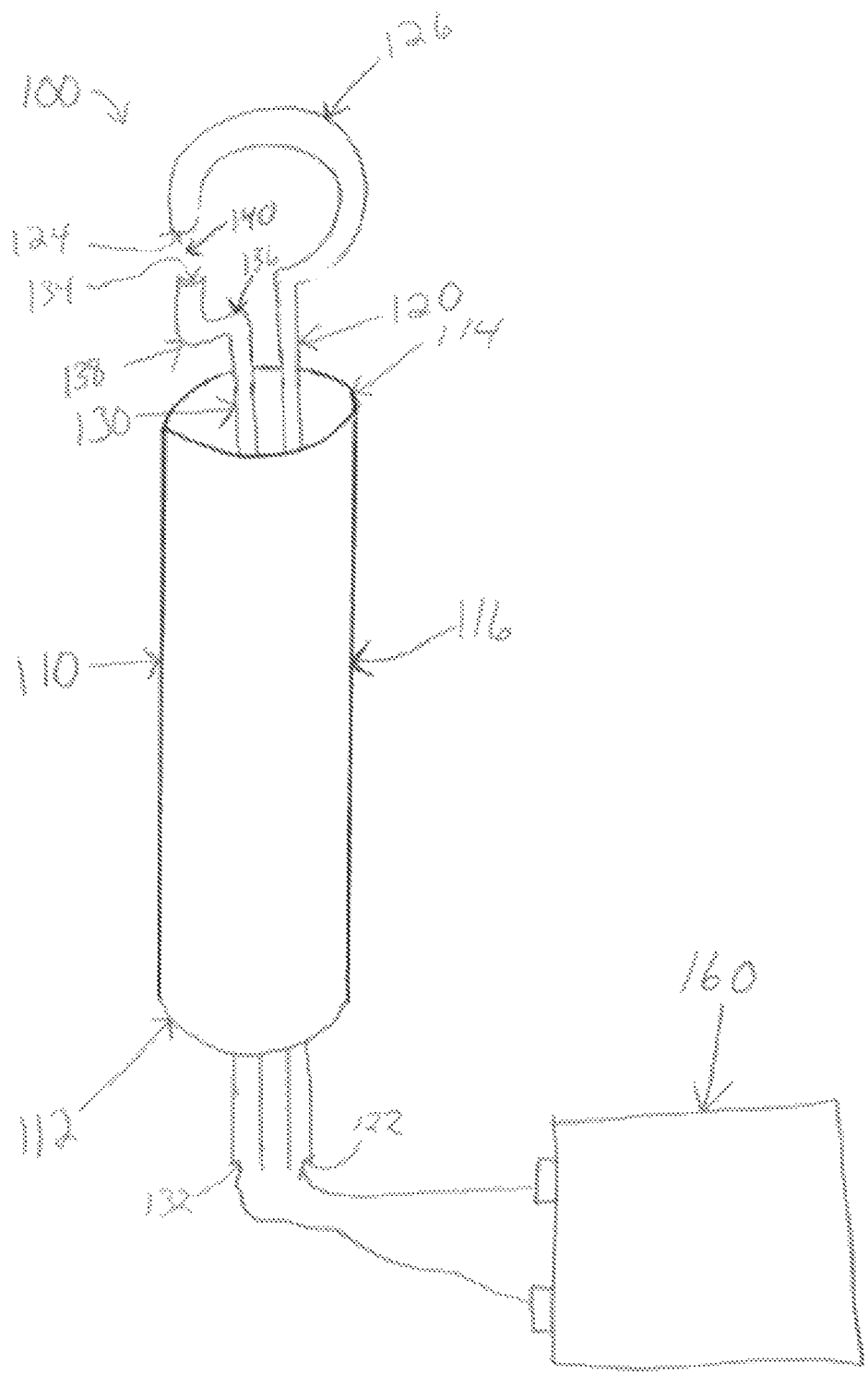
FIG. 16: Illustration of the first embodiment of an IVC filter retrieval device with a closing member and a grabbing member that are not in direct contact, where the IVC filter retrieval device includes a computer or microcontroller.

Referring now to FIG. 16, the IVC filter retrieval device 100 is depicted in a position in which there is a gap 140 between the distal closing member end 134 and the distal grabbing member end 124, so as to create an open loop. This embodiment of the IVC filter retrieval device 100 further includes a computer or microcontroller 160 configured to control when and how the grabbing member 120 and the closing member 130 form the closed loop or form a gap 140 therebetween. The use of a computer or microcontroller 160 may provide simplicity and reliability to the closing and opening of the grabbing member 120 and closing member 130.

Figure 17:
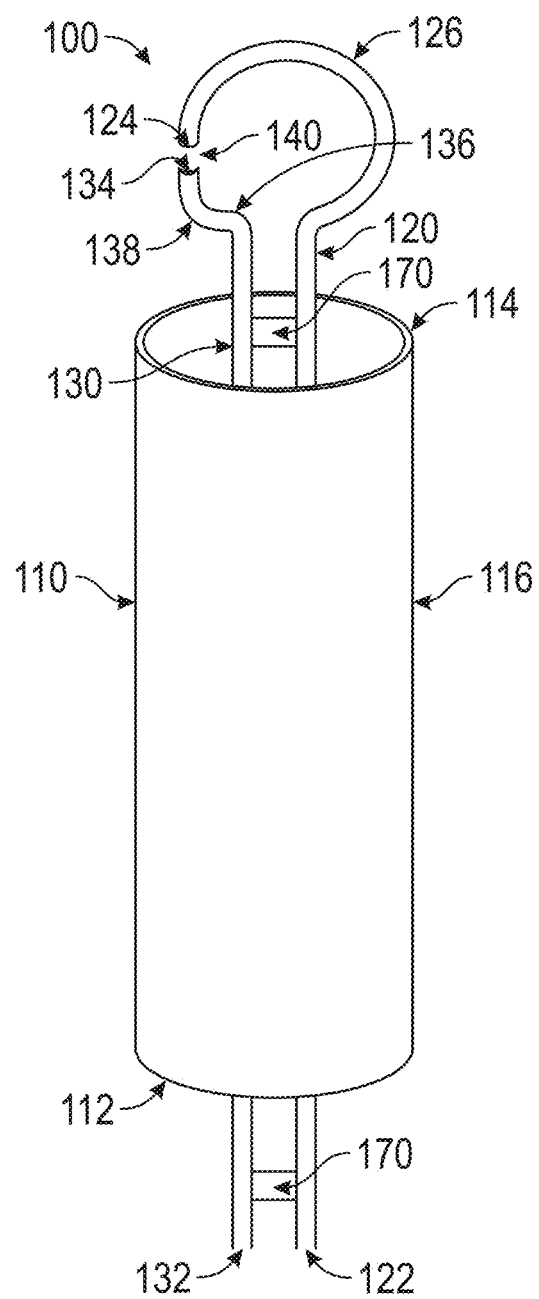
FIG. 17: Illustration of the first embodiment of an IVC filter retrieval device with a closing member and a grabbing member that are not in direct contact, where the IVC filter retrieval device includes spacers.

Referring now to FIG. 17, the IVC filter retrieval device 100 may further include spacers 170 disposed between the closing member 130 and the grabbing member 120. The spacers 170 may be composed of any suitable material, and the spacers 170 may serve the purpose of keeping a defined minimum distance between the closing member 130 and the grabbing member 120, allowing the distal ends 124, 134 to more easily align.

Referring now to FIGS. 18-28, an alternative embodiment of the IVC filter retrieval device 200 is depicted. The IVC filter retrieval device 200 is substantially similar to the IVC filter retrieval device 100, and therefore has corresponding reference numbers in the figures, but the IVC filter retrieval device 200 omits the feature of the curved protrusion 138 that extends from the distal closing member portion 136 as depicted in FIGS. 1-17. In this embodiment of the IVC filter retrieval device 200, the curved protrusion 138 is not present on the distal closing member portion 236. Instead, the distal closing member portion 236 is simply an elongated portion of the closing member 230. The omission of the curved protrusion 138 may allow for easier alignment of the closing member 230 and the grabbing member 220, depending on the user's preference. The omission of the curved protrusion 138 also allows for the loop formed between the grabbing member 230 and the closing member 220 to be smaller, because the grabbing member portion 226 does not need to extend as far in order for the grabbing member distal end 224 to align with the closing member distal end 234. In this embodiment, the user may have an easier time aligning the distal grabbing member end 224 and the distal closing member end 234, though may have a more difficult time grasping an IVC filter 150 because of the reduced size of the grabbing member portion 226.

Figure 18:
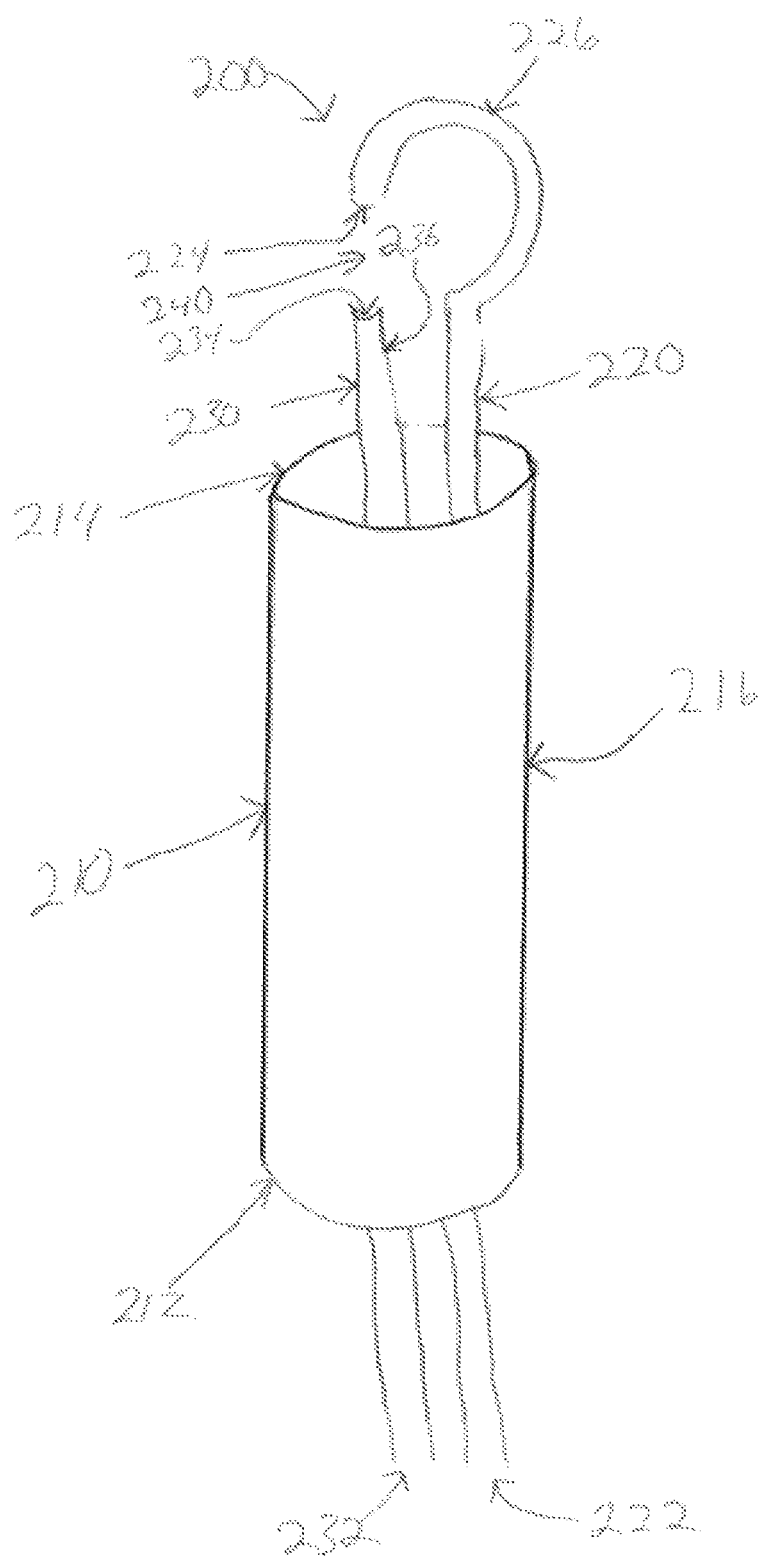
FIG. 18: Illustration of a second embodiment of an IVC filter retrieval device with a closing member and a grabbing member that are not in direct contact.
Figure 19:
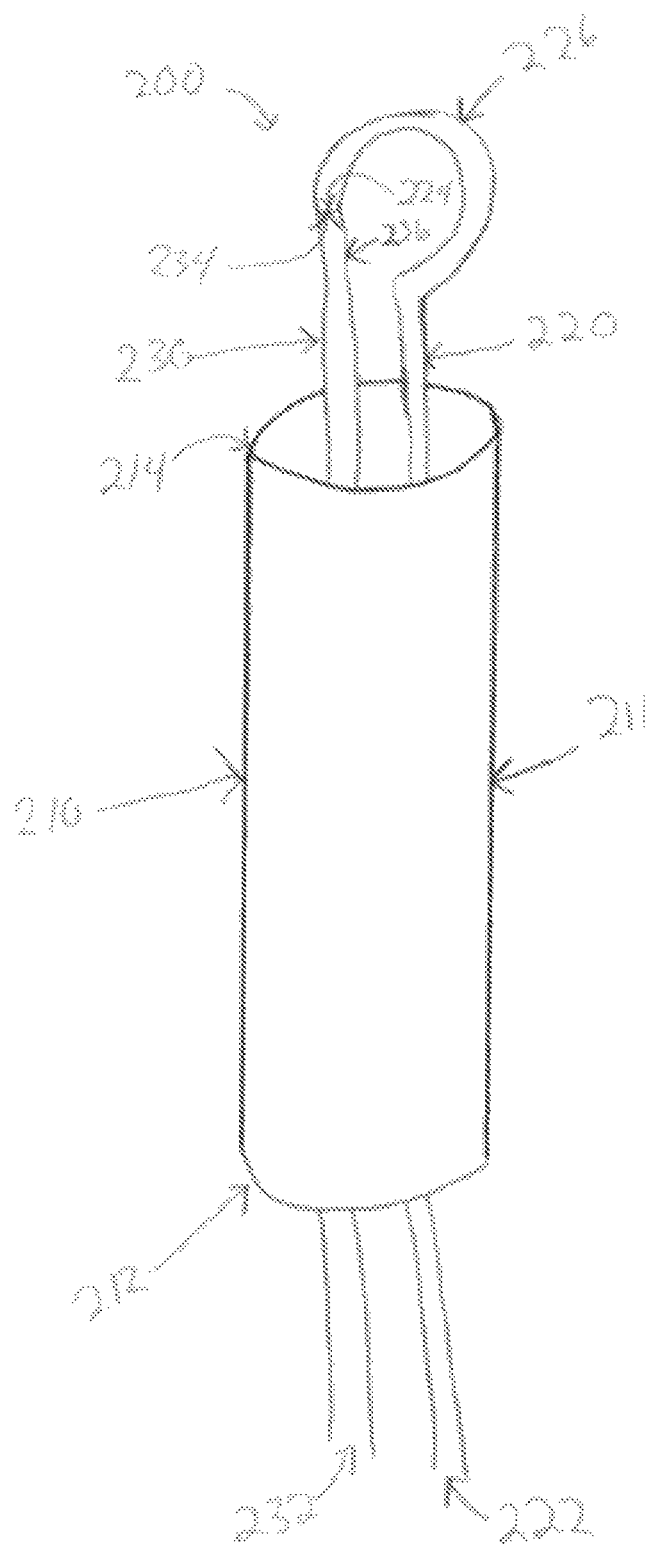
FIG. 19: Illustration of the second embodiment of an IVC filter retrieval device with a closing member and a grabbing member that are in direct contact at their respective distal ends.
Figure 20:
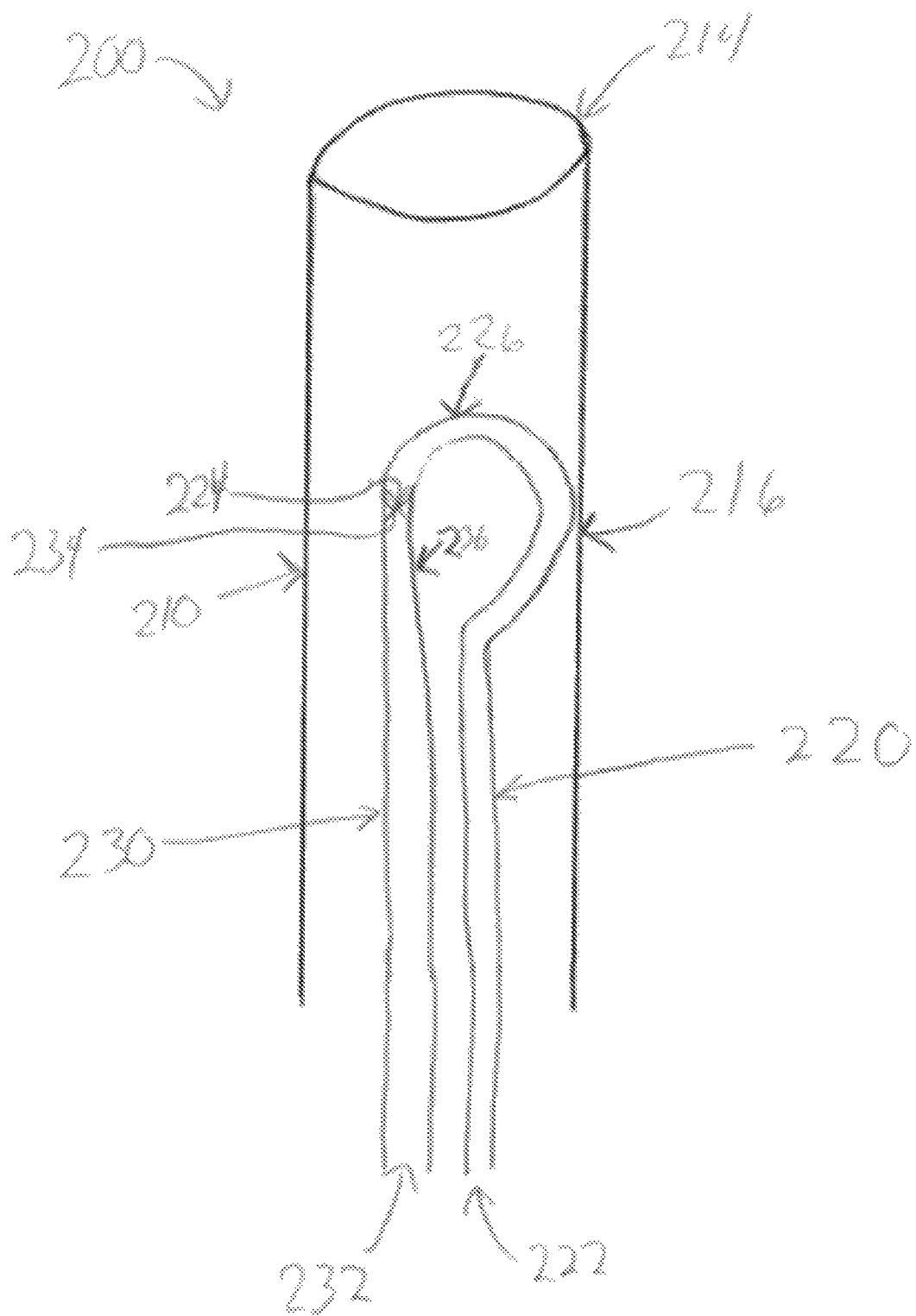
FIG. 20: Illustration of the second embodiment of an IVC filter retrieval device with a closing member and a grabbing member that are in direct contact at their respective distal ends, and the closing member and the grabbing member are retracted within the sheath.
Figure 21:
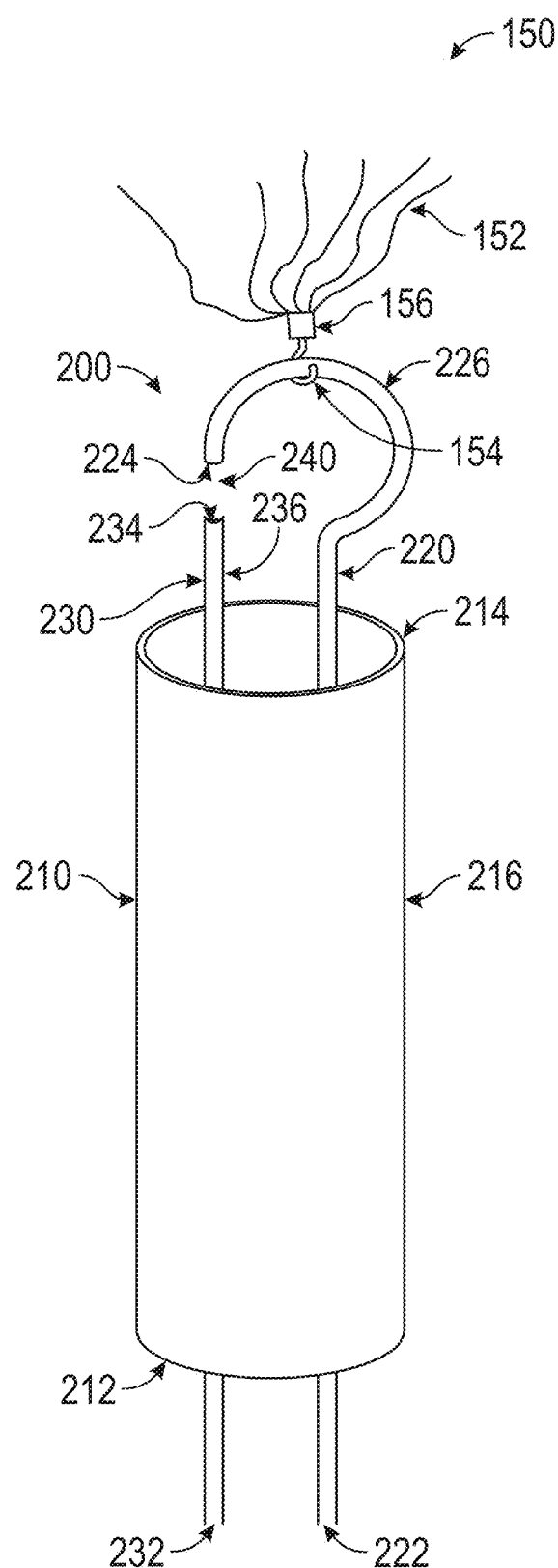
FIG. 21: Illustration of the second embodiment of an IVC filter retrieval device with a closing member and a grabbing member that are not in direct contact, where the grabbing member is positioned in proximity to the hook of an IVC filter.
Figure 22:
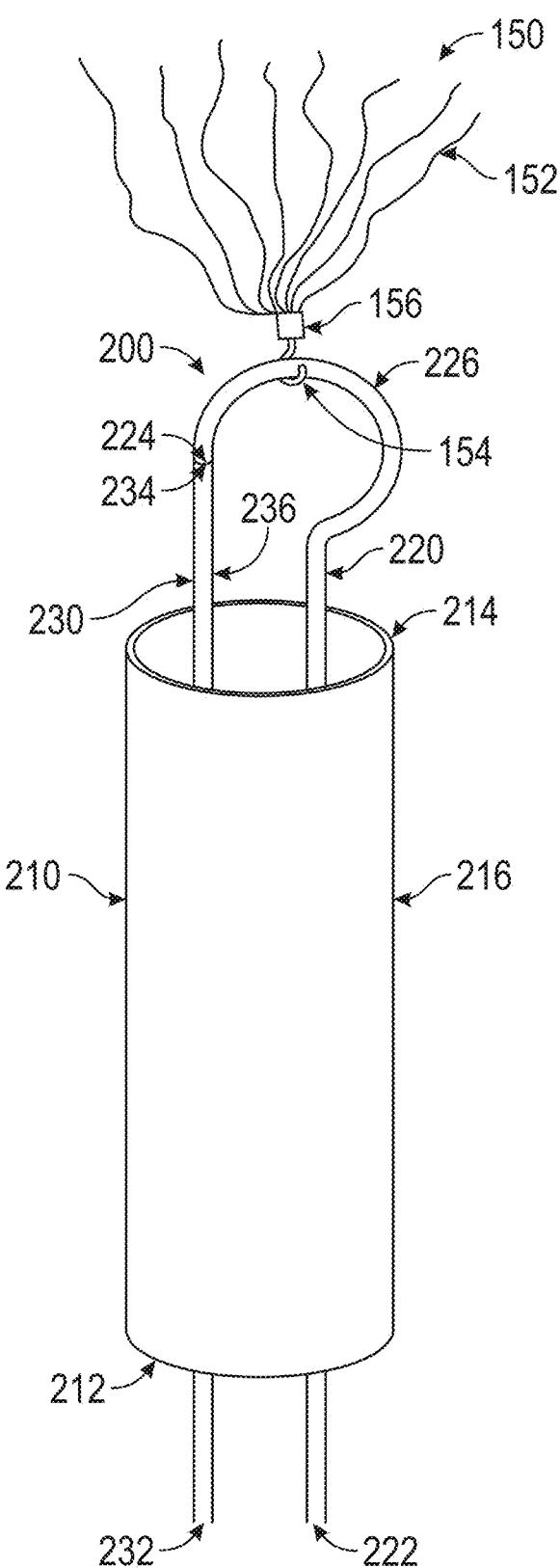
FIG. 22: Illustration of the second embodiment of an IVC filter retrieval device with a closing member and a grabbing member that are in direct contact at their respective distal ends, where the grabbing member is positioned in proximity to the hook of an IVC filter.
Figure 23:
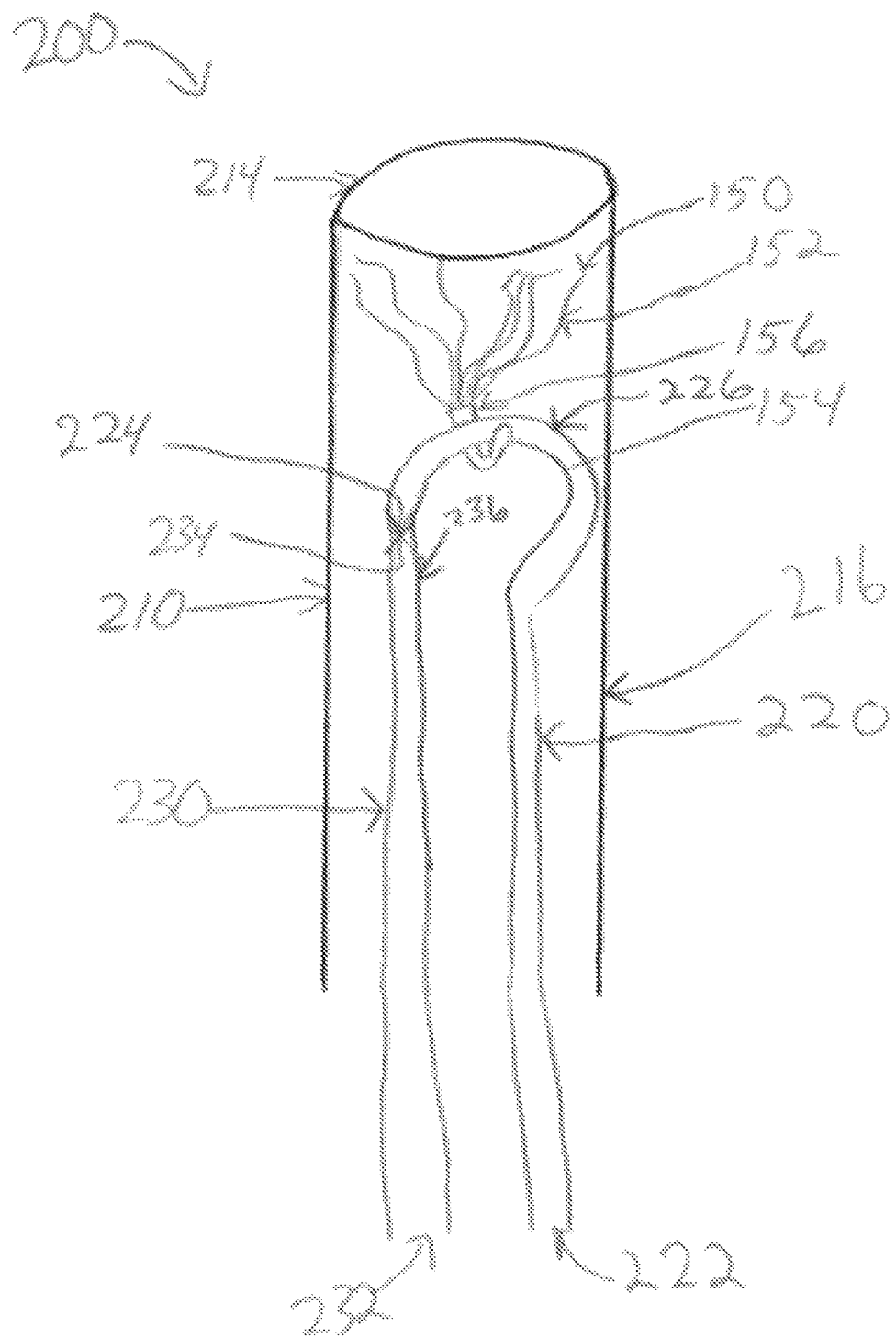
FIG. 23: Illustration of the second embodiment of an IVC filter retrieval device with a closing member and a grabbing member that are in direct contact at their respective distal ends, where the grabbing member is grabbing the hook of an IVC filter, and where the grabbing member and the closing member are retracted into the sheath.

In FIG. 18, the IVC filter retrieval device 200 without a curved protrusion 138 is depicted in an open loop configuration, where there is a gap 240 between the distal grabbing member end 224 and the distal closing member end 234. In FIG. 19, the IVC filter retrieval device 200 without a curved protrusion 138 is depicted in a closed loop configuration, where the distal grabbing member end 224 is in direct contact with the distal closing member end 234. In FIG. 20, the IVC filter retrieval device 200 is depicted retracted into the sheath 210 while in the closed loop configuration. In FIG. 21, the IVC filter retrieval device 200 is depicted in an open loop configuration where the grabbing member 220 is grabbing an IVC filter 150 by the IVC filter hook 154. In FIG. 22, the IVC filter retrieval device 200 is depicted still grabbing the IVC filter 150 by the IVC filter hook 154, but in a closed loop configuration where the distal grabbing member end 224 is in direct contact with the distal closing member end 234 so as to secure the IVC filter hook 154 within a closed loop. In FIG. 23, the IVC filter retrieval device 200 is depicted in the closed loop configuration with the IVC filter hook 154 secured, and while retracted into the sheath 210.

Figure 24:
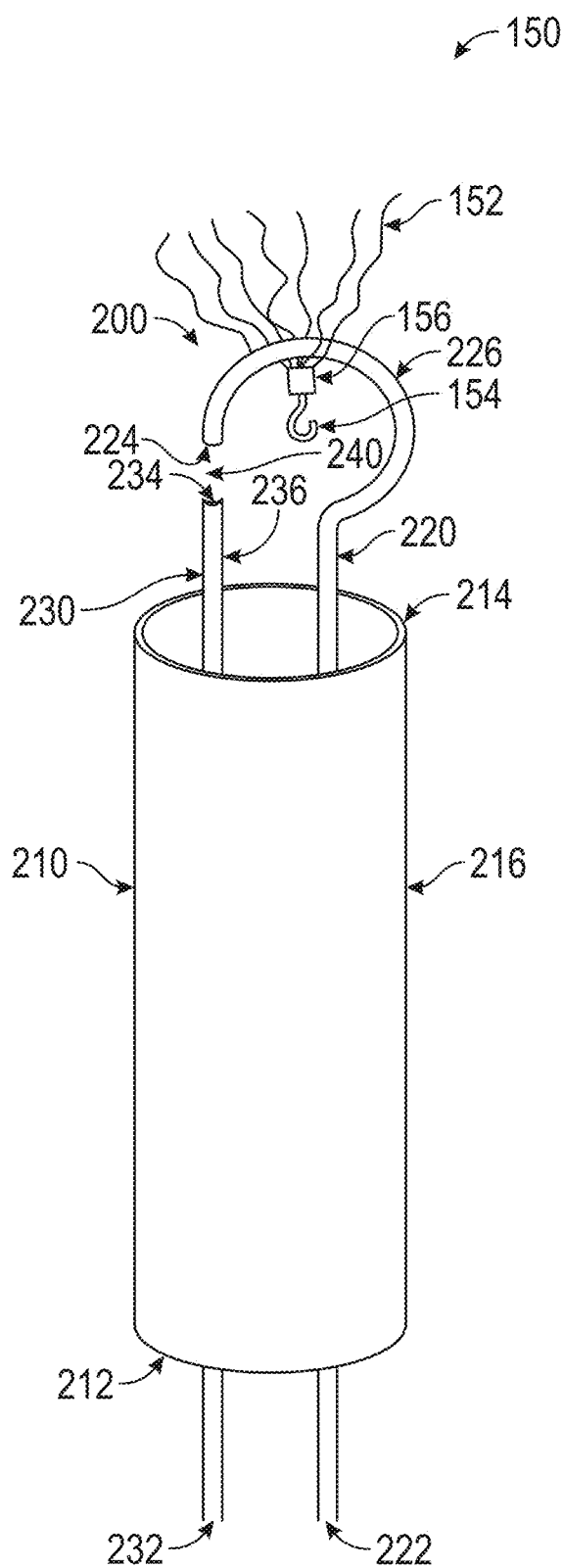
FIG. 24: Illustration of the second embodiment of an IVC filter retrieval device with a closing member and a grabbing member that are not in direct contact, where the grabbing member is positioned near the neck of an IVC filter.
Figure 25:
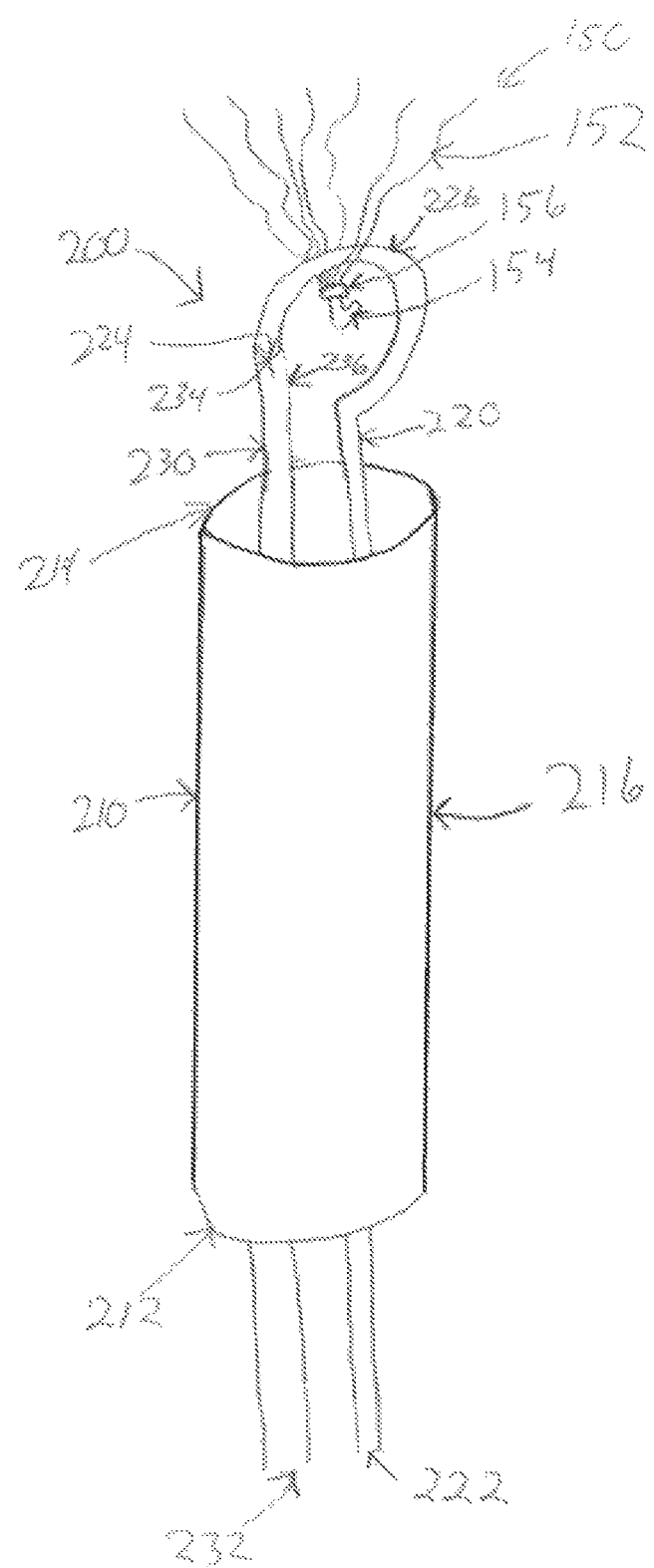
FIG. 25: Illustration of the second embodiment of an IVC filter retrieval device with a closing member and a grabbing member that are in direct contact at the respective distal ends, and the grabbing member is positioned near the neck of an IVC filter.
Figure 26:
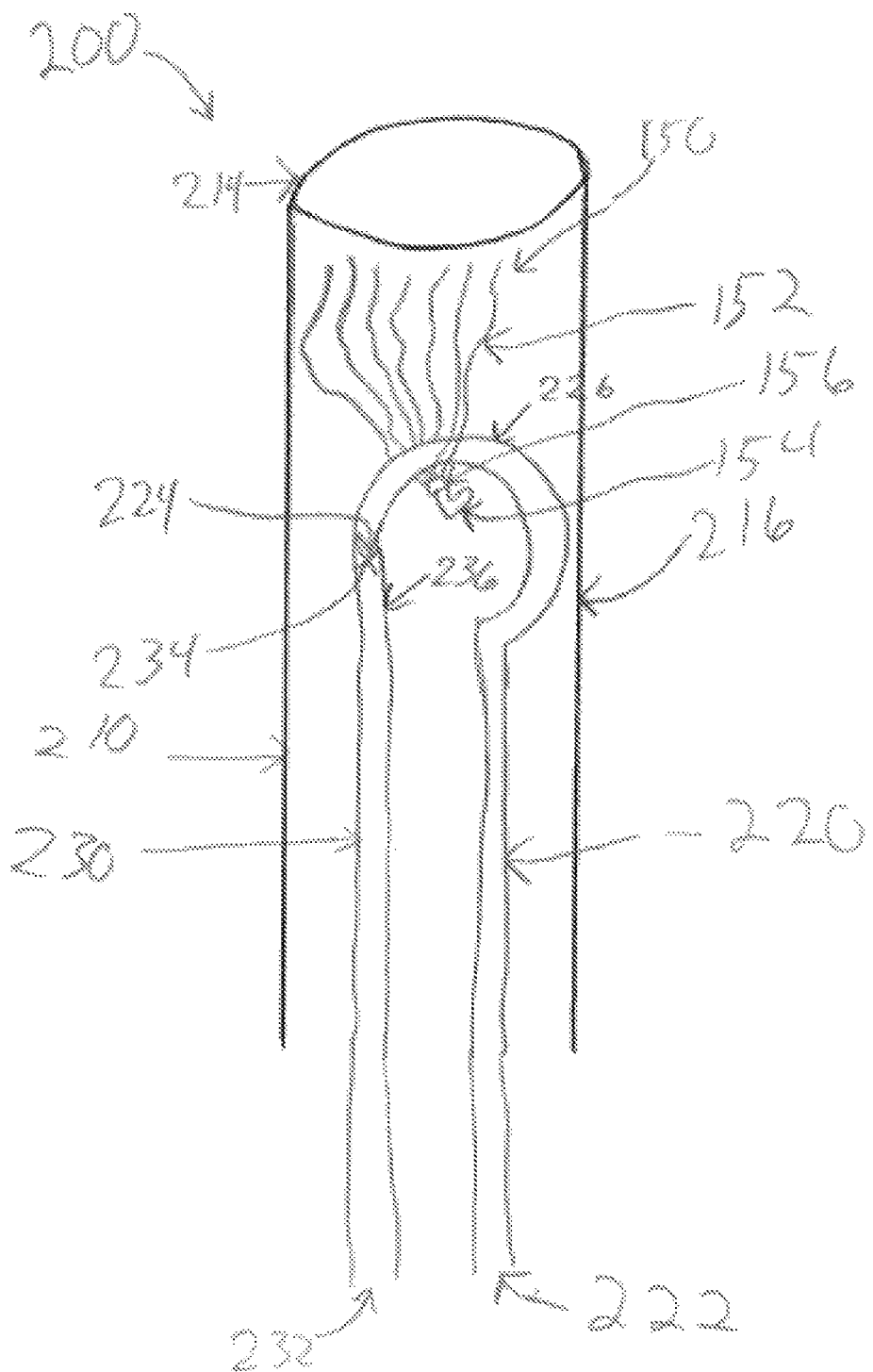
FIG. 26: Illustration of the second embodiment of an IVC filter retrieval device with a closing member and a grabbing member that are in direct contact at their respective distal ends, where the grabbing member is grabbing the neck of an IVC filter, and where the grabbing member and the closing member are retracted within the sheath.

In FIG. 24, the IVC filter retrieval device 200 is depicted grabbing an IVC filter 150 by the IVC filter neck 156 instead of the IVC filter hook 154. As discussed above, this may sometimes be necessary because of the inaccessibility of the IVC filter hook 154, and advantageously, the ability of the IVC filter retrieval device 200 to retrieve an IVC filter 150 by the IVC filter neck 156 reduces the number of situations in which an IVC filter 150 cannot be removed. The ability of the IVC filter retrieval device 200 to create an open loop and also a closed loop allows for the IVC filter retrieval device 200 to grasp and secure an IVC filter neck 156. In FIG. 25, the IVC filter retrieval device 200 is depicted grabbing an IVC filter 150 by the IVC filter neck 156 and being in a closed loop configuration in which the distal grabbing member end 224 is in direct contact with the distal closing member end 234 so as to prevent dislodgment of the IVC filter 150. In FIG. 26, the IVC filter retrieval device 200 is depicted grabbing the IVC filter neck 156, in a closed loop configuration, and retracted into the sheath 210.

Figure 27:
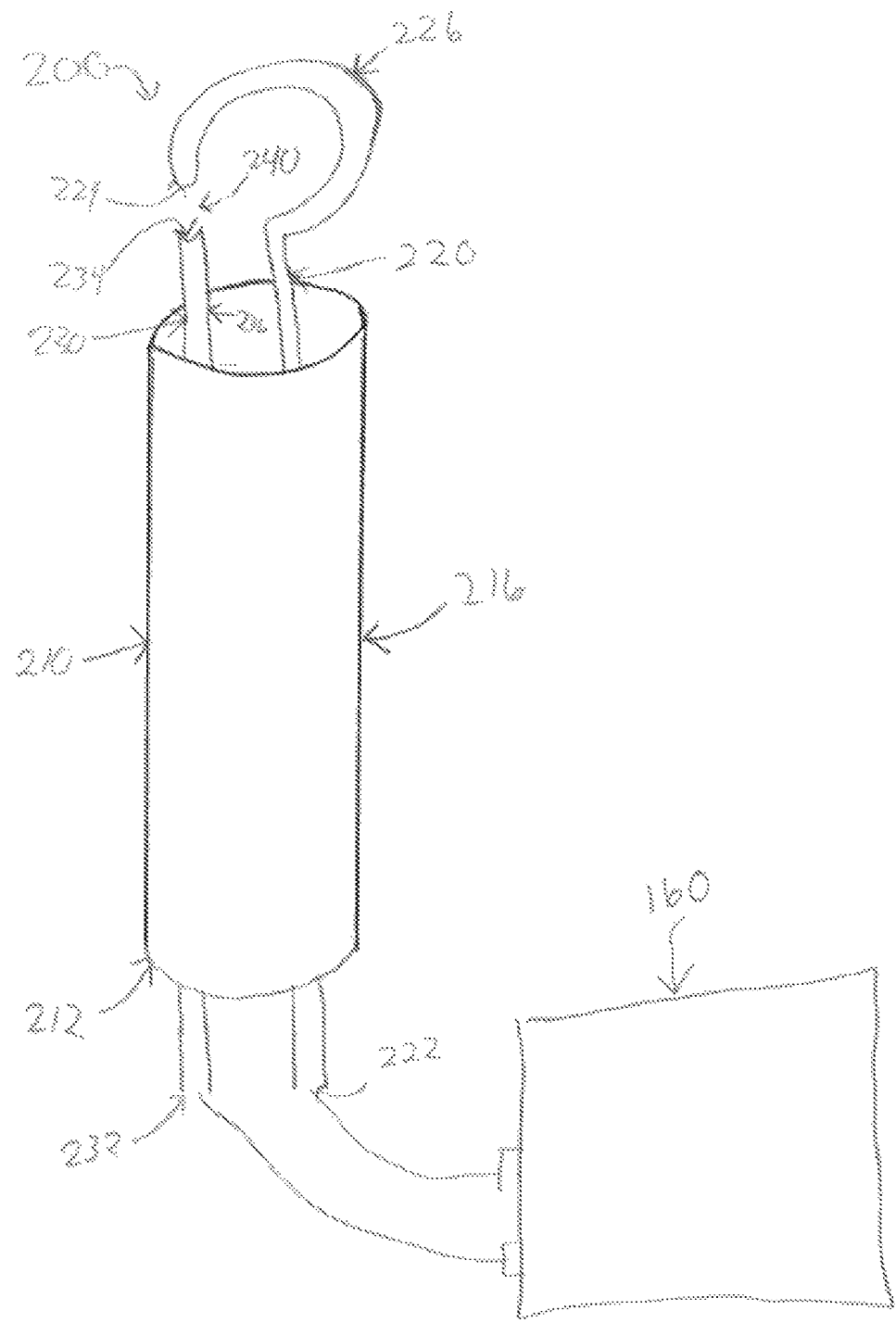
FIG. 27: Illustration of the second embodiment of an IVC filter retrieval device with a closing member and a grabbing member that are not in direct contact at their respective distal ends, where the IVC filter retrieval device includes a computer or microcontroller.

Referring now to FIG. 27, the IVC filter retrieval device 200, without the curved protrusion 138, is depicted with a computer or microcontroller 160. As described above, the computer or microcontroller 160 may simplify and provide reliability to the opening and closing of the grabbing member 220 and the closing member 230.

Figure 28:
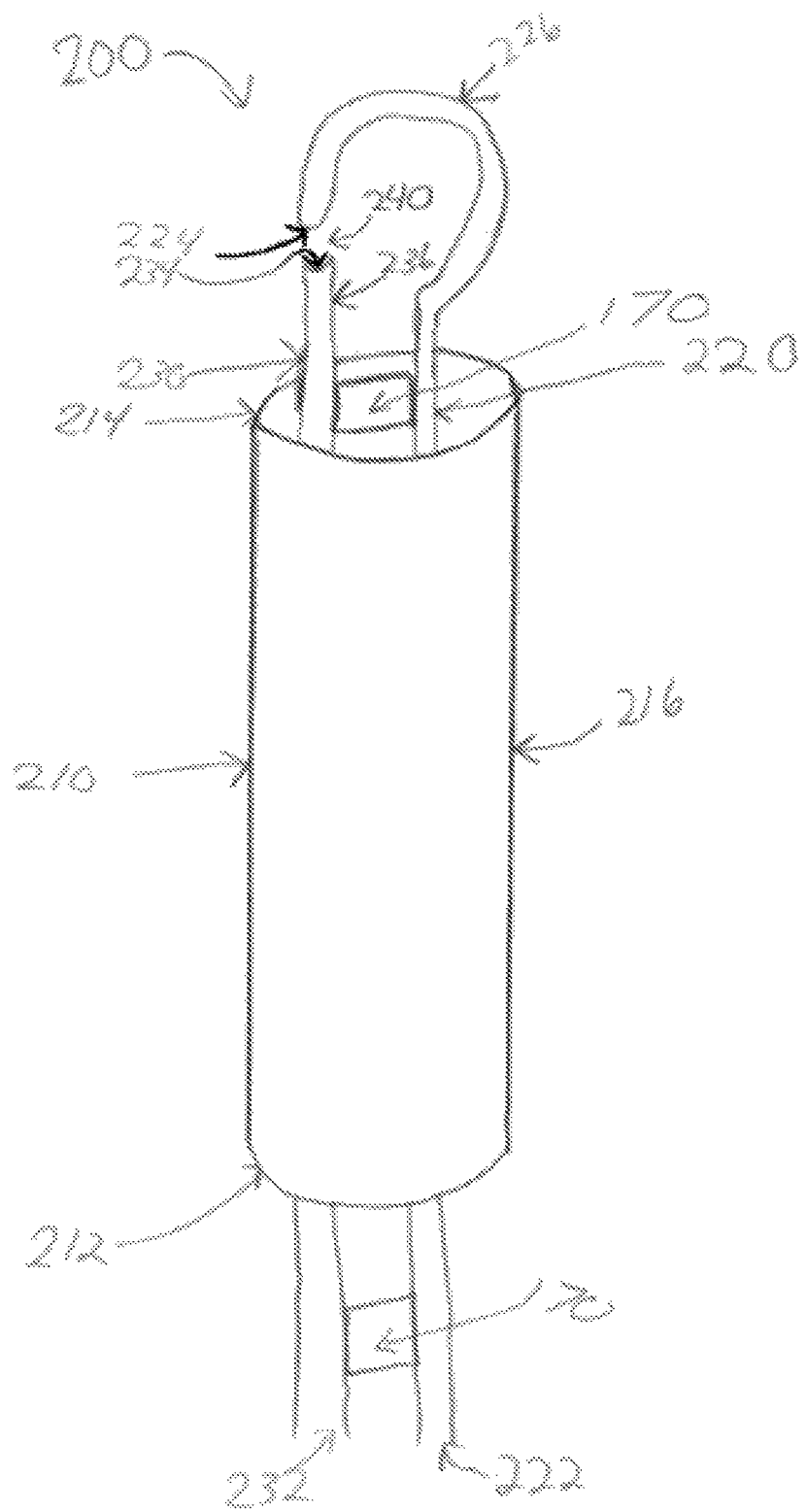
FIG. 28: Illustration of the second embodiment of an IVC filter retrieval device with a closing member and a grabbing member that are not in direct contact, where the IVC filter retrieval device includes spacers.

Referring now to FIG. 28, the IVC filter retrieval device 200, without the curved protrusion 138, is depicted with spacers 170 between the grabbing member 220 and the closing member 230. As described above, the spacers 170 serve the purpose of keeping a defined minimum distance between the closing member 230 and the grabbing member 220, allowing the distal ends 224, 234 to more easily align.

Figure 4:
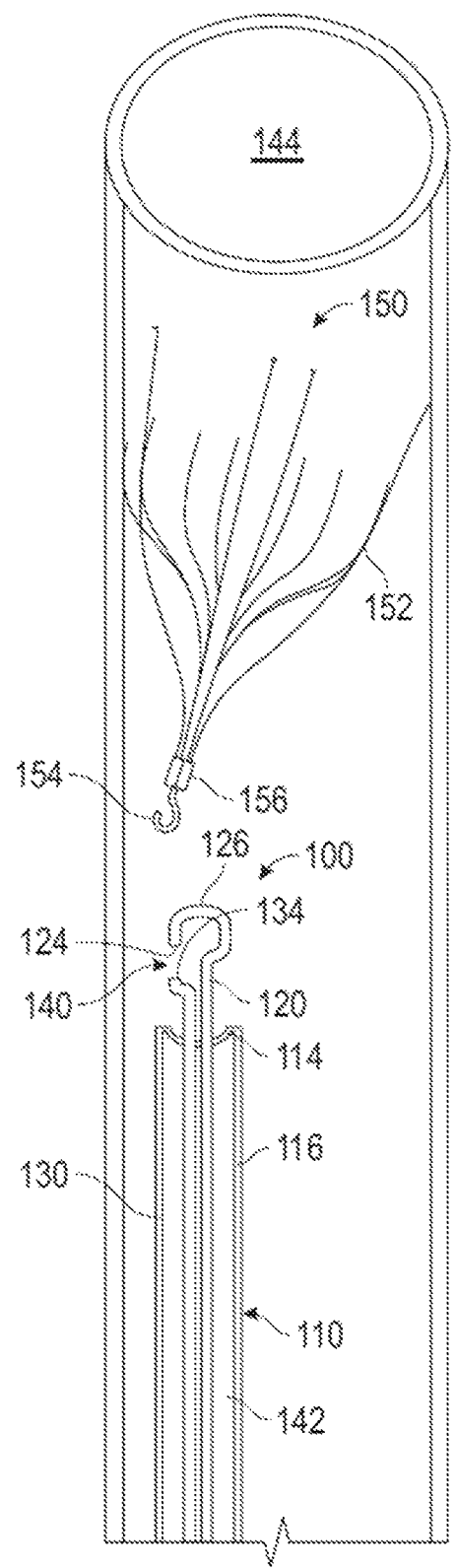
FIG. 4: Illustration of the first embodiment of an IVC filter retrieval device within a blood vessel being positioned near an IVC filter.
Figure 5:
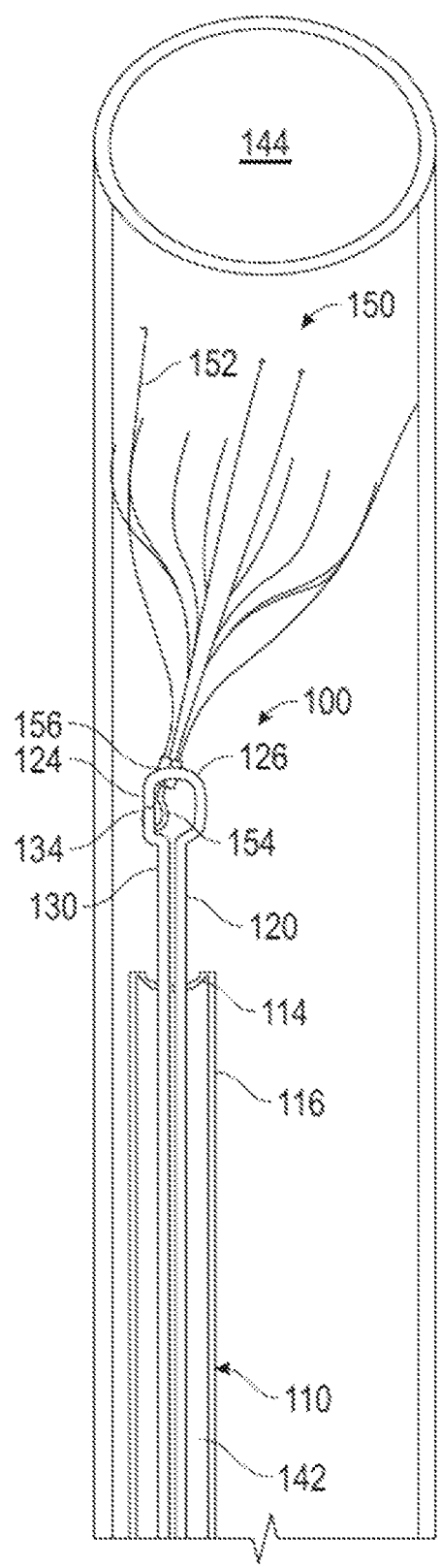
FIG. 5: Illustration of the first embodiment of an IVC filter retrieval device with a closing member and a grabbing member that are engaged, where the grabbing member is grabbing the neck of an IVC filter.

Referring now to FIGS. 4-5, the IVC filter retrieval device 100 is depicted within a vessel 144, where in FIG. 4 the IVC filter retrieval device 100 is being progressed toward the IVC filter 150, and in FIG. 5, the IVC filter retrieval device 100 has secured the IVC filter 150 in a closed loop. The IVC filter retrieval device 100 (and also the alternative embodiment of the IVC filter retrieval device 200 without the curved protrusion 138) can be utilized in different ways to achieve the removal of an IVC filter 150 from a blood vessel 144. As one non-limiting example, the IVC filter retrieval device 100 may first be inserted into a vessel 144. Once the IVC filter retrieval device 100 is deployed in a vessel 144 nearby an IVC filter 150, the grabbing member 120 and the closing member 130 may each be twisted, pushed, and/or pulled in order to first grab an IVC filter 150 with the grabbing member 120, and then secure the IVC filter 150 on the grabbing member 120 by bringing the grabbing member 120 into direct contact with the closing member 130. The IVC filter 150 can be grabbed by the IVC filter hook 154, the IVC filter neck 156, the IVC filter leg 152, or any other part of the IVC filter 150 that allows for the IVC filter 150 to be securely retrieved by the IVC filter retrieval device 100. Once the IVC filter 150 is secured by the distal grabbing member portion 126, a closed loop may be formed between the grabbing member 120 and the closing member 130 to hold the IVC filter 150 in place, and the closed loop (i.e., the distal grabbing member portion 126 and the distal closing member portion 136) may be retracted into the lumen 142 of the sheath 110. The IVC filter retrieval device 100 may then be removed from the vessel 144, with the IVC filter 150 secured inside the sheath 110, without complication.

In an alternative embodiment of a method for removing an IVC filter 150 from a blood vessel 144, the IVC filter retrieval device 100 is used to grab the IVC filter 150 with the grabbing member 120, but the grabbing member 120 and the closing member 130 are not closed to form a closed loop prior to retracting the grabbing member 120, with the IVC filter 150 attached thereto, into the sheath 110. Once the distal grabbing member portion 126 is retracted into the sheath 110 with the IVC filter 150 attached, a closed loop may be formed between the grabbing member 120 and the closing member 130 within the sheath 110. However, it is not strictly necessary that a closed loop ever be formed. In some cases, it may be unnecessary to close the grabbing member 120 and the closing member 130 together to form a closed loop in order to retrieve an IVC filter 150 from a blood vessel 144.

Certain embodiments of the devices and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the devices and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. An IVC filter retrieval device comprising:
   a sheath defining a lumen and extending from a sheath proximal end to a sheath distal end;
   a grabbing member movable within the lumen, wherein the grabbing member extends from a distal grabbing member end to a proximal grabbing member end, and includes a distal grabbing member portion; and
   a closing member movable within the lumen, wherein the closing member extends from a distal closing member end to a proximal closing member end;
   wherein the grabbing member is configured to move between an extended grabbing position in which the distal grabbing member end protrudes from the sheath at the sheath distal end, and a retracted grabbing position in which the distal grabbing member end is disposed within the sheath;
   wherein the closing member is configured to move between an extended closing position in which the distal closing member end protrudes from the sheath at the sheath distal end, and a retracted closing position in which the closing member is disposed within the sheath;
   wherein the grabbing member and the closing member are movable to create a closed loop wherein the distal grabbing member end is in direct contact with the distal closing member end;
   wherein the grabbing member and the closing member are movable to create an open loop wherein the distal grabbing member end is disposed a distance away from the distal closing member end, the distance defining a gap;
   wherein a distal closing member portion comprises a curved protrusion causing the distal closing member end to protrude outward a distance from an axis defined by the proximal closing member end; and
   wherein a loop formed between the grabbing member and the closing member has a loop radius larger than a radius of the sheath.

2. The IVC filter retrieval device of claim 1, wherein the distal grabbing member end is rotatable by rotating the proximal grabbing member end.

3. The IVC filter retrieval device of claim 1, wherein the closing member comprises a distal closing member portion having a curved protrusion causing the distal closing member end to protrude outward a distance from an axis defined by the proximal closing member end.

4. The IVC filter retrieval device of claim 1, further comprising a computer or microcontroller configured to control movement of the grabbing member and the closing member so as to form the open loop or the closed loop between the grabbing member and the closing member.

5. The IVC filter retrieval device of claim 1, further comprising a spacer between the closing member and the grabbing member configured to maintain a minimum distance between the closing member and the grabbing member.

6. The IVC filter retrieval device of claim 1, wherein each of the distal grabbing member end and the distal closing member end includes a magnet configured to attract each other.

7. The IVC filter retrieval device of claim 1, wherein the distal grabbing member portion has a curvature, defining an arc or semicircle.

8. The IVC filter retrieval device of claim 1, wherein the distal grabbing member portion is a hook.

9. The IVC filter retrieval device of claim 1, wherein the distal grabbing member portion defines a partial square or a partial rectangle.

10. The IVC filter retrieval device of claim 1, wherein the grabbing member and the closing member are movable to create the closed loop while each of the grabbing member and the closing member protrudes from the sheath at the sheath distal end.

11. A method of retrieving an IVC filter from a blood vessel, the method comprising:
   inserting an IVC filter retrieval device into the blood vessel in proximity to the IVC filter;
   moving an arcuate end of a first elongated member of the device so as to grab the IVC filter and capture the IVC filter on the arcuate end;
   creating a closed loop between the first elongated member and a second elongated member of the device so as to secure the IVC filter for retrieval;
   retracting the first elongated member and the second elongated member into a sheath; and
   retrieving the IVC filter retrieval device from the blood vessel so as to retrieve the IVC filter;
   wherein a radius of the closed loop is larger than a radius of the sheath.

12. The method of retrieving an IVC filter from a blood vessel of claim 11,
   wherein the first elongated member and the second elongated member are independently movable through independent movement of respective proximal ends of the first elongated member and the second elongated member.

13. The method of claim 11, wherein the IVC filter is grabbed at an IVC filter neck instead of an IVC filter hook.

\* \* \* \* \*